US009095557B2

(12) United States Patent
Stöhr

(10) Patent No.: US 9,095,557 B2
(45) Date of Patent: *Aug. 4, 2015

(54) ANTICONVULSANT COMBINATION THERAPY

(71) Applicant: UCB Pharma GmbH, Monheim (DE)

(72) Inventor: Thomas Stöhr, Monheim (DE)

(73) Assignee: UCB PHARMA GMBH, Monheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/080,440

(22) Filed: Nov. 14, 2013

(65) Prior Publication Data

US 2014/0088168 A1 Mar. 27, 2014

Related U.S. Application Data

(63) Continuation of application No. 12/304,023, filed as application No. PCT/EP2007/005304 on Jun. 15, 2007, now Pat. No. 8,735,356.

(60) Provisional application No. 60/813,967, filed on Jun. 15, 2006.

(30) Foreign Application Priority Data

Oct. 12, 2006 (EP) .................................... 06021469
Oct. 12, 2006 (EP) .................................... 06021470
Nov. 22, 2006 (EP) .................................... 06024241

(51) Int. Cl.
A61K 31/19 (2006.01)
A61K 31/35 (2006.01)
A61K 31/40 (2006.01)
A61K 31/53 (2006.01)
A61K 31/55 (2006.01)
A61K 38/04 (2006.01)
A61K 38/05 (2006.01)
A61K 45/06 (2006.01)
A61K 31/165 (2006.01)
A61K 31/195 (2006.01)
A61K 31/4015 (2006.01)
A61K 31/4166 (2006.01)

(52) U.S. Cl.
CPC .............. A61K 31/19 (2013.01); A61K 31/165 (2013.01); A61K 31/195 (2013.01); A61K 31/35 (2013.01); A61K 31/40 (2013.01); A61K 31/4015 (2013.01); A61K 31/4166 (2013.01); A61K 31/53 (2013.01); A61K 31/55 (2013.01); A61K 38/04 (2013.01); A61K 38/05 (2013.01); A61K 45/06 (2013.01)

(58) Field of Classification Search
CPC ... A61K 31/165; A61K 31/19; A61K 31/195; A61K 31/35; A61K 31/40; A61K 31/4015; A61K 31/4166; A61K 31/53; A61K 31/55; A61K 38/04; A61K 38/05; A61K 45/06
USPC ................................................ 514/17.7, 424
See application file for complete search history.

(56) References Cited

U.S. PATENT DOCUMENTS

| 4,303,673 | A | 12/1981 | Biedermann et al. |
| 4,510,082 | A | 4/1985 | Gesellchen et al. |
| 4,513,009 | A | 4/1985 | Roques et al. |
| 4,533,657 | A | 8/1985 | Morgan |
| 4,618,708 | A | 10/1986 | Roques et al. |
| 4,707,468 | A | 11/1987 | Yoshino et al. |
| 5,378,729 | A | 1/1995 | Kohn et al. |
| 5,508,266 | A | 4/1996 | Fink |
| 5,536,853 | A | 7/1996 | Spellmeyer et al. |
| 5,585,358 | A | 12/1996 | Bialer et al. |
| 5,654,301 | A | 8/1997 | Kohn et al. |
| 5,656,267 | A | 8/1997 | Sagen et al. |
| 5,760,038 | A | 6/1998 | Murugesan et al. |
| 5,773,475 | A | 6/1998 | Kohn |
| 5,780,589 | A | 7/1998 | Lazarus et al. |
| 5,866,585 | A | 2/1999 | Fogel |
| 5,885,999 | A | 3/1999 | Elliott et al. |
| 6,001,876 | A | 12/1999 | Singh |
| 6,028,102 | A | 2/2000 | Bialer et al. |
| 6,037,324 | A | 3/2000 | Schwender et al. |
| 6,048,899 | A | 4/2000 | Kohn et al. |
| 6,083,941 | A | 7/2000 | Farb |
| 6,083,951 | A | 7/2000 | Bradbury |
| 6,103,732 | A | 8/2000 | Amberg et al. |

(Continued)

FOREIGN PATENT DOCUMENTS

DE 195 33 023 A1 4/1996
EP 0555537 8/1993

(Continued)

OTHER PUBLICATIONS

Abbott, F.V., et al. (1995) "The formalin test: scoring properties of the first and second phases of the pain response in rats" Pain, 60:91-102.
Abdulla,F.A., et al. (2002) "Changes in Na+ Channel Currents of Rat Dorsal Root Ganglion Neurons Following Axotomy and Axotomy-Induced Autotomy" J. Neurophysiol, 88:2518-2529.
Aigner, T., et al. (2002) "Molecular pathology and pathobiology of osteoarthritic cartilage" Cell. Mol. Life Sci. 59: 5-18.
Akiba, I., et al. (2003). "Stable Expression and Characterization of Human PN1 and PN3 Sodium Channels." Receptors and Channels. 9:291-299.
Albensi, B.C., et al. (2004). "Why Do Many NMDA Anatagonists Fail, While Others are Safe and Effective at Blocking Excitotoxicity Associated with Dementia and Acute Injury?" Am. J. Alzheimer's Disease & Other Dementias. 19(5):269-274.
Amir, R., et al. (2006). "The Role of Sodium Channels in Chronic Inflammatory and Neuropathic Pain." The Journal of Pain. 7(5 Suppl. 3):S1-S29.

(Continued)

Primary Examiner — Julie Ha
(74) Attorney, Agent, or Firm — Harness, Dickey & Pierce P.L.C.

(57) ABSTRACT

The present invention is directed to a pharmaceutical composition comprising a Compound (a) of a class of peptide Compounds and at least one further Compound (b) for the prevention, alleviation or/and treatment of epileptic seizures.

22 Claims, 8 Drawing Sheets

(56) References Cited

U.S. PATENT DOCUMENTS

| | | | |
|---|---|---|---|
| 6,114,390 | A | 9/2000 | Engel et al. |
| 6,126,939 | A | 10/2000 | Eisenbach-Schwartz et al. |
| 6,133,261 | A | 10/2000 | Harris |
| 6,180,611 | B1 | 1/2001 | Montana et al. |
| 6,277,825 | B1 | 8/2001 | Olivera et al. |
| 6,331,637 | B1 | 12/2001 | Chan et al. |
| 6,492,553 | B1 | 12/2002 | Hulme et al. |
| 6,596,756 | B1 | 7/2003 | Goldstein et al. |
| 6,737,408 | B1 | 5/2004 | Balasubramanium et al. |
| RE38,551 | E | 7/2004 | Kohn |
| 6,803,481 | B2 | 10/2004 | Selve |
| 6,884,910 | B2 | 4/2005 | Harris |
| 6,903,130 | B1 | 6/2005 | Lamberty et al. |
| 7,041,704 | B2 | 5/2006 | Burgard et al. |
| 7,090,985 | B2 | 8/2006 | Lynch et al. |
| 7,148,378 | B2 | 12/2006 | Harris |
| 7,186,859 | B2 | 3/2007 | Harris |
| 7,416,864 | B2 | 8/2008 | Stoehr |
| 7,427,601 | B2 | 9/2008 | Stoehr |
| 7,687,553 | B2 | 3/2010 | Beyreuther et al. |
| 7,718,161 | B2 | 5/2010 | Stoehr |
| 7,794,987 | B2 | 9/2010 | Stoehr |
| 7,820,857 | B2 | 10/2010 | Stoehr et al. |
| 7,875,652 | B2 | 1/2011 | Selve |
| 7,884,134 | B2 | 2/2011 | Riedner et al. |
| 8,008,351 | B2 | 8/2011 | Scheller et al. |
| 8,053,476 | B2 | 11/2011 | Selve |
| 8,338,641 | B2 | 12/2012 | Stohr et al. |
| 8,536,137 | B2 | 9/2013 | Beyreuther et al. |
| 2002/0052418 | A1 | 5/2002 | Shirvan et al. |
| 2002/0169174 | A1 | 11/2002 | Chackalamannil et al. |
| 2003/0216466 | A1 | 11/2003 | Scheuerman et al. |
| 2004/0101582 | A1 | 5/2004 | Wolicki |
| 2004/0106147 | A1 | 6/2004 | Lynch et al. |
| 2004/0204388 | A1 | 10/2004 | Lynch et al. |
| 2004/0204495 | A1 | 10/2004 | Shirvan et al. |
| 2004/0220077 | A1 | 11/2004 | Selve |
| 2005/0013856 | A1 | 1/2005 | Trivedi et al. |
| 2005/0043675 | A1 | 2/2005 | Pastore et al. |
| 2005/0085423 | A1 | 4/2005 | Selve |
| 2005/0169982 | A1 | 8/2005 | Almarssoo et al. |
| 2005/0209163 | A1 | 9/2005 | Stoehr |
| 2005/0227961 | A1 | 10/2005 | Kucharik et al. |
| 2005/0261204 | A1 | 11/2005 | Stohr |
| 2005/0277579 | A1 | 12/2005 | Krishnan et al. |
| 2005/0277596 | A1 | 12/2005 | Stohr |
| 2005/0288234 | A1 | 12/2005 | Stohr |
| 2006/0004069 | A1 | 1/2006 | Momose et al. |
| 2006/0009384 | A1 | 1/2006 | Rudd et al. |
| 2006/0046957 | A1 | 3/2006 | Beyreuther et al. |
| 2006/0100157 | A1 | 5/2006 | Rauschkolb-Loffler et al. |
| 2006/0135437 | A1 | 6/2006 | Stoehr et al. |
| 2006/0194873 | A1 | 8/2006 | Choi et al. |
| 2006/0252749 | A1 | 11/2006 | Stohr |
| 2007/0042969 | A1 | 2/2007 | Rauschkolb-Loffler et al. |
| 2007/0043120 | A1 | 2/2007 | Beyreuther et al. |
| 2007/0048372 | A1 | 3/2007 | Beyreuther et al. |
| 2007/0054962 | A1 | 3/2007 | Selve |
| 2007/0197657 | A1 | 8/2007 | Beyreuther et al. |
| 2007/0293476 | A1 | 12/2007 | Smith-Swintosky et al. |
| 2008/0027137 | A1 | 1/2008 | Riedner et al. |
| 2008/0096872 | A1 | 4/2008 | Friedman |
| 2008/0280835 | A1 | 11/2008 | Beyreuther et al. |
| 2008/0287545 | A1 | 11/2008 | Scheller et al. |
| 2009/0018197 | A1 | 1/2009 | Rudd et al. |
| 2009/0018198 | A1 | 1/2009 | Stohr |
| 2009/0241205 | A1 | 9/2009 | Beyreuther et al. |
| 2010/0029543 | A1 | 2/2010 | Beyreuther et al. |
| 2010/0099770 | A1 | 4/2010 | Selve |
| 2010/0240576 | A1 | 9/2010 | Stoehr |
| 2010/0256179 | A1 | 10/2010 | Stohr et al. |
| 2010/0256241 | A1 | 10/2010 | Stoehr et al. |
| 2010/0260716 | A1 | 10/2010 | Stohr et al. |
| 2010/0273714 | A1 | 10/2010 | Stoehr |
| 2010/0324144 | A1 | 12/2010 | Heers et al. |
| 2011/0082211 | A1 | 4/2011 | Selve |
| 2011/0130350 | A1 | 6/2011 | Riedner et al. |
| 2012/0225119 | A1 | 9/2012 | Beyreuther et al. |
| 2012/0238614 | A1 | 9/2012 | Stohr |
| 2013/0251803 | A1 | 9/2013 | Cawello et al. |
| 2013/0251813 | A1 | 9/2013 | Cawello et al. |
| 2014/0066515 | A1 | 3/2014 | Heers et al. |
| 2014/0128377 | A1 | 5/2014 | Stoehr |
| 2014/0128378 | A1 | 5/2014 | Stoehr |

FOREIGN PATENT DOCUMENTS

| | | |
|---|---|---|
| EP | 0885186 | 12/1998 |
| EP | 0997147 | 5/2000 |
| EP | 1077945 | 2/2001 |
| EP | 1160248 | 12/2001 |
| EP | 1243263 | 9/2002 |
| EP | 1486205 | 12/2004 |
| EP | 1486206 | 12/2004 |
| EP | 1537862 | 6/2005 |
| EP | 1541138 | 6/2005 |
| EP | 1579858 | 9/2005 |
| EP | 1604655 A1 | 12/2005 |
| EP | 1688137 | 8/2006 |
| EP | 1754476 A1 | 2/2007 |
| EP | 2037965 A2 | 3/2009 |
| EP | 2735338 A1 | 5/2014 |
| JP | 5443981 B2 | 3/2014 |
| WO | WO-9015069 A2 | 12/1990 |
| WO | WO-9214706 A1 | 9/1992 |
| WO | WO-9221648 A1 | 12/1992 |
| WO | WO-9530645 A1 | 11/1995 |
| WO | WO-9611209 A1 | 4/1996 |
| WO | WO-9632100 | 10/1996 |
| WO | WO-9738980 A1 | 10/1997 |
| WO | WO-9738981 A1 | 10/1997 |
| WO | WO-9809953 A2 | 3/1998 |
| WO | WO-9902146 A1 | 1/1999 |
| WO | WO-9907413 A1 | 2/1999 |
| WO | WO-9916444 A1 | 4/1999 |
| WO | WO-9923078 A2 | 5/1999 |
| WO | WO-9943309 A2 | 9/1999 |
| WO | WO-9956761 A1 | 11/1999 |
| WO | WO-0021509 A2 | 4/2000 |
| WO | WO-0051586 A2 | 9/2000 |
| WO | WO-0117976 A1 | 3/2001 |
| WO | WO-01/62726 A2 | 8/2001 |
| WO | WO-0178762 A1 | 10/2001 |
| WO | WO-0213766 A2 | 2/2002 |
| WO | WO-0215922 A2 | 2/2002 |
| WO | WO-0215937 A2 | 2/2002 |
| WO | WO-0224698 A1 | 3/2002 |
| WO | WO-0242256 A2 | 5/2002 |
| WO | WO-0250051 | 6/2002 |
| WO | WO-02060863 A1 | 8/2002 |
| WO | WO-02074297 A1 | 9/2002 |
| WO | WO-02074784 A2 | 9/2002 |
| WO | WO-02076979 A1 | 10/2002 |
| WO | WO-02087548 A1 | 11/2002 |
| WO | WO-02088664 A2 | 11/2002 |
| WO | WO-03000642 A2 | 1/2003 |
| WO | WO-03039520 A1 | 5/2003 |
| WO | WO-03106482 A1 | 12/2003 |
| WO | WO-2004014895 A1 | 2/2004 |
| WO | WO-2004039365 A1 | 5/2004 |
| WO | WO-2004043926 A1 | 5/2004 |
| WO | WO-2004046178 A2 | 6/2004 |
| WO | WO-2004060353 A1 | 7/2004 |
| WO | WO-2004066987 A2 | 8/2004 |
| WO | WO-2004066990 A2 | 8/2004 |
| WO | WO-2004091585 A1 | 10/2004 |
| WO | WO-2004100871 A2 | 11/2004 |
| WO | WO-2005040355 A2 | 5/2005 |
| WO | WO-2005053557 A1 | 6/2005 |
| WO | WO-2005053667 A1 | 6/2005 |
| WO | WO-2005092313 A1 | 10/2005 |
| WO | WO-2005099740 A1 | 10/2005 |
| WO | WO-2005110405 A1 | 11/2005 |
| WO | WO-2005120539 A2 | 12/2005 |

(56) References Cited

FOREIGN PATENT DOCUMENTS

| WO | WO-2006019978 A2 | 2/2006 |
|---|---|---|
| WO | WO-2006037574 A1 | 4/2006 |
| WO | WO-2006079547 A2 | 8/2006 |
| WO | WO-2007/144195 A2 | 12/2007 |

OTHER PUBLICATIONS

Andurkar, S.V., et al. (1999) "The anticonsulvant activities of n-benzyl 3-methoxypropionamides." Bioorg. Med. Chem. 7(11):2381-2389.
Arendt-Nielsen, L. (1997) "Induction and assessment of experimental pain from human skin, muscle, and viscera" Proc. 8th World Congress of Pain (Jensen et al., eds., IASP Press, Seattle).
Arnt, J., et al. (1984). "Prolonged Treatment with the Specific 5-HT-Uptake Inhibitor Citalopram: Effect on Dopaminergic and Serotonergic Functions." Pol. Journal of Pharmacol. Pharm. 36:221-230.
Arnér, S., et al. (1988). "Lack of Analgesic Effect of Opioids on Neuropathic and Idiopathic Forms of Pain." Pain. 33:11-23.
Arroyo, S. (2003) "Safety of SPM 927 in subjects with epilepsy and neuropathic pain" Poster presented at AES Scientific Exhibit, Dec. 5-10, 2003.
Backonja, M.M. (2002). "Use of Anticonvulsants for Treatment of Neuropathic Pain." Neurology. 59:S14-S17.
Backonja, M.M. (2003). "Defining Neuropathic Pain." Anesth. Analg. 97:785-790.
Barton, M.E., et al. (2001) "Pharmacological characterization of the 6 Hz psychomotor seizure model of partial epilepsy" Epilepsy Research, 47(3):217-227 (PubMed Abstract Only).
Ben-Menachem, E. (2005). "A dose-response, placebo-controlled trial using lacosamide as adjunctive therapy in subjects with partial seizures." Presented at 26th International Epilepsy Congress, Aug 28-Sep 1, 2005. Schwarz Biosciences. 1-15.
Ben-Menachem, E., et al. (2005) "Efficacy and safety of adjunctive oral lacosamide for the treatment of partial-onset seizures in patients with epilepsy" Presented at American Academy of Neurology 57th Annual Meeting. Schwarz Biosciences, 1.
Bennett, A.D., et al. (1988) "A peripheral mononeuropathy in rat that produces disorders of pain sensation like those seen in man" Pain, 33(1):87-107 (PubMed Abstract Only).
Bennett, A.D., et al. (2000) "Alleviation of mechanical and thermal allodynia by cgrp8-37 in a rodent model of chronic central pain" Pain, 86:163-175.
Berenbaum, M.C. (1989) "What is Synergy?" Pharmacological Review, 1981(41):93-141.
Beyak, M.J., et al. (2004) "Two TTX-Resistant Na+ currents in mouse colonic dorsal root ganglia neurons and their role in colitis-induced hyperexcitability" American Journal of Physiol. Gastrointest. Liver Physiol., 287:G845-G855.
Beyreuther, (2004) "Pharmacology of SPM 927 and its relevance to clinical practice for neuropathic pain" Presented at Visiongain Pain Management, Schwarz Biosciences.1-31.
Beyreuther, B. et al. (2006) "Antinociceptive efficacy of lacosamide in a rat model for painful diabetic neuropathy" European Journal of Pharmacology. 539:64-70.
Beyreuther, B. et al. (2006). "Effects of lacosamide as compared to other analgesics: a responder analysis in the streptozotocin rat model for diabetic neuropathic pain." Poster 618 presented at American Pain Society, 2006. Schwarz Biosciences. 1. (abstract at http://www.ampainsoc.org/db2/abstract/view?poster_id=2637#618).
Beyreuther, B. et al. (2006). "Lacosamide displays antinociceptive effects in a rat model for musculoskelatal pain induced by TNF." Poster 625 presented at American Pain Society, 2006. Schwarz Bioscience. 1. (abstract at http://www.ampainsoc.org/db2/abstract/view?poster_id=2643#625).
Beyreuther, B. et al. (2006). "Lacosamide displays antinociceptive effects in rat models for arthritis pain." Poster 626 presented at American Pain Society, 2006. Schwarz Biosciences. 1. (abstract at http://www.ampainsoc.org/db2/abstract/ view?poster_id=2644#626).

Beyreuther, B. et al. (2007) "Antinociceptive efficacy of lacosamide in the monosodium iodoacetate rat model for osteoarthritis pain" Arthritis Research and Therapy. 9:R14.
Beyreuther, B. et al. (2007) "Lacosamide: a review of preclinical properties" CNS Drug Reviews. 13(1):21-42.
Beyreuther, B., et al. (2004). "SPM 927 displays potent antinococeptive effects in rat models for inflammatory and neuropathic pain." Presented at Neuropathic Pain, May 13-14, 2004. Schwarz Biosciences. 1.
Beyreuther, B., et al. (2005). "Lacosamide displays antinociceptive effects in a rat model for diabetic neuropathic pain." Presented at World Congress on Pain, Aug. 21-26, 2005. Schwarz Biosciences. 1.
Beyreuther, B., et al. (2005). "Lacosamide displays antinociceptive effects in a rat model for tumor-induced cancer pain and chemotherapy-induced pain" Presented at World Congress on Pain, Aug. 21-26, 2005. Schwarz Biosciences. 1.
Bialer, M. et al. (2001) "Progress report on new antiepileptic drugs: a summary of the Fifth Eilat Conference (EILAT V)" Epilepsy Research. 43:11-58.
Bialer, M. et al. (2002) "Progress report on new antiepileptic drugs: a summary of the Sixth Eilat Conference (EILAT VI)" Epilepsy Research. 51:31-71.
Bilsky, E. J. et al. (2000) "Enkephalin glycopeptide analogues produce analgesia with reduced dependence liability" ournal of Medicinal Chemistry. 43:2586-2590.
Biton, V. (2006) "Multicenter, double-blind, double-dummy trial investigating safety, tolerability and pharmacokinetics of intravenous lacosamide (SPM 927) in subjects with partial seizures" Presented at European Congress on Epileptology, Jul. 2006, Schwarz Biosciences.1-17.
Biton, V. et al. (2003) "Safety and efficacy of SPM 927 during the initial phase of an extension trial in subjects with partial seizures"American Epilepsy Society, Epilepsia. 44(9):259. Abstract No. 2.241.
Biton, V. et al. (2004) "Safety and tolerability of lacosamide solution for infusion" Poster presented at AES Scientific Exhibit, Dec. 3-7, 2004. Schwarz Biosciences. 1.
Biton, V. et al. (2005) "Safety and tolerability of intravenous lacosamide as replacement for oral lacosamide in subjects with partial seizures" Poster P02.148 presented at International Epilepsy Congress, Aug. 28-Sep. 1, 2005. Schwarz Biosciences. 1.
Blackburn-Munro, G. et al. (2002) "A comparison of the antinociceptive effects of voltage-activated Na+ channel blockers in the formalin test" European Journal of Pharmacology. 445:231-238.
Blair, N.T. et al. (2002) "Roles of tetrodotoxin (TTX)-sensitive Na+ current, TTX-resistant Na+ current, and Ca2+ current in the action potentials of nociceptive sensory neurons" The Journal of Neuroscience. 22(23):10277-10290.
Blair, N.T. et al. (2003) "Role of Tetrodotoxin-Resistant Na+ current slow inactivation in adaptation of action potential firing in small-diameter dorsal root ganglion neurons" The Journal of Neuroscience. 23(32):10338-10350.
Borowicz, K.K et al. (2000) "The AMPA/Kainate Receptor Antagonist, LY 300164, increases the anticonvulsant effects of diazepam" Naunyn Schmiedebergs Arch Pharmacol. 361(6):629-635. (PubMed Abstract Only).
Borowicz, K.K. et al. (2002) "Effect of gabapentin on the anticonvulsant activity of antiepileptic drugs against electroconvulsions in mice: an isobolographic analysis" Epilepsia. 43(9):956-963. (PubMed Abstract Only).
Boulton, A.J.M. (2003) "Treatment of symptomatic diabetic neuropathy" Diabetes Metabolism Research Review. 19:S16-S21.
Bourgeois, B.F. (1988) "Anticonvulsant potency and neurotoxicity of valproate alone and in combination with carbamazepine or phenobarbital" Clinical Neuropharmacol. 11(4):348-359. (PubMed Abstract Only).
Bourgeois, B.F. et al. (1988) "Combined administration of carbamazepine and phenobarbital: effect on anticonvulsant activity and neurotoxicity" Epilepsia. 29(4):482-487. (PubMed Abstract Only).
Brandt, K.D. (2001) Principles of internal medicine, Harrison's 15th ed. New York, McGraw-Hill. pp. 1987-1994.

(56) References Cited

OTHER PUBLICATIONS

Bretschneider, M. et al. (2006) "A multi-center, open-label, follow-on trial to assess the long-term safety and efficacy of lacosamide in subjects with painful distal diabetic neuropathy" Poster No. 766 Presented at the American Pain Society Annual Meeting, 2006. Schwarz Bioscience. 1.

Bril, V. (2001) "Status of current clinical trials in diabetic polyneuropathy" The Canadian Journal of Neurological Science. 28:191-198.

Brodie, M.J. (1996) "Lamotrigine—an update" The Canadian Journal of Neurological Science. 23(Suppl. 2):S6-S9.

Brodie, M.J. (2001) "Do we need any more new antiepileptic drugs?" Epilepsy Research. 45(1-3):3-6. (PubMed Abstract Only).

Bunney, W.E. et al. (1982) "A second generation catecholamine hypothesis" Pharmacopsychiatry. 15:111-115.

Béguin, C., et al. (2003). "Functionalized Amido Ketones: New Anticonvulsant Agents." Bioorganic & Medicinal Chemistry. 11:4275-4285.

Béguin, C., et al. (2004). "N-Substituted Amino Acid N'-benzylamides: synthesis, anticonvulsant, and metabolic activity." Bioorganic & Medicinal Chemistry. 12:3079-3096.

Caliendo, G. et al. (2005) "Derivatives as 5HT1A receptor ligands-past and present" Current Medicinal Chemistry. 12:1721-1753.

Calvino, B. et al. (1987) "Parallel clinical and behaviorural studies of adjuvant-induced arthritis in the rat: possible relationship with 'chronic pain'" Behavioural Brain Research. 24:11-29.

Cannon, S.C. (2006) "Pathomechanisms in channelopathies of skeletal muscle and brain" Annu. Rev. Neurosci. 29:387-415. (PubMed Abstract Only).

Casey, D.E. et al. (2003) "Effect of divalproex combined with alanzapine or risperidone in patients with an acute exacerbation of schizophrenia" Neuropsychopharmacology. 28:182-192.

Casey, D.E. et al. (2009) "Divalproex ER combined with olanzapine or risperidone for treatment of acute exacerbations of schizophrenia" Neuropsychopharmacology 34:1330-1338.

Cattails (2001) http://erb.archive.org/web/20050326134029/www2.marshfieldclinic.org/cattails/01/mayjun/arthritis/asp Accessed Jan. 3, 2011.

Cawello, W. et al. (2003) "No influence of the new antiepileptic drug SPM 927 on the ECG time intervals QTc and PR" American Epilepsy Society, Epilepsia. 44(Suppl. 9):95. Abstract No. 1.265.

Cawello, W. et al. (2004) "Food does not affect the pharmacokinetics of SPM 927" American Epilepsy Society, Epilepsia. 45(Suppl. 7):307. Abstract No. 2.342.

Chen, H.S. (2006) "The chemical biology of clinically tolerated NMDA receptor antagonists" Journal of Neurochemistry. 97:1611-1626.

Chevrier, P. et al. (2004) "Differential Modulation of Nav1.7 and Nav1.8 peripheral nerve sodium channels by the local anesthetic lidocaine" British Journal of Pharmacology. 142:576-584.

Chipkin, S., et al., (2005), "How to select and combine oral agents for patients with type 2 diabetes mellitus", The American Journal of Medicine, 118 (5A), 4S-13S.

Choi, D. et al. (1996) "Synthesis and anticonvulsant activities of N-benzyl-2-acetamidopropionamide derivatives" J. Med. Chem. 39:1907-1916.

Christensen, M.D. et al. (1996) "Mechanical and thermal allodynia in chronic central pain following spinal cord injury" Pain. 68:97-107.

Citrome, L. (2003) "Schizophrenia and valproate" Psychopharmacology Bulletin. 37(Suppl. 2):74-88.

Citrome, L. et al. (2007) "Risperidone alone versus risperidone plus valproate in the treatment of patients with schizophrenia and hostility" International Clinical Psychopharmacology. 22(6):356-362.

Collins, S.L. et al. (2000) "Antidepressants and Anticonvulsants for Diabetic Neuropathy and Postherpetic Neuralgia: A Quantitative Systemic Review" Journal of Pain and Symptom Management. 20:449-458.

Colpaert, F.C. et al. (1982) "Further evidence validating adjuvant arthritis as an experimental model of chronic pain in the rat" Life Sciences. 31:67-75.

Combe, R. et al. (2004) "The monosodium iodoacetate model of osteoarthritis: a model of chronic nociceptive pain in rats?" Neuroscience Letters. 370:236-240.

Crofford, L.J. (2009) "Fibromyalgia" American College of Rheumatology. 1-4.

Cummins, T.R. et al. (2004) "Electrophysiological properties of mutant Nav1.7 sodium channels in a painful inherited neuropathy" Journal of Neuroscience. 24(38):8232-8236.

Daniels, A. et al. (2005) "Long-term safety and efficacy of lacosamide as adjunctive therapy in subjects with partial seizures: 96-week follow-up" Poster presented at AES Scientific Exhibit, Dec. 2-5, 2005. Schwarz Biosciences.1.

Deckers, C.L. et al. (2000) "Selection of Antiepileptic Drug Polytherapy Based on Mechanisms of Action: the Evidence Reviewed" Epilepsia. 41(11):1364-1374. (PubMed Abstract Only).

Decosterd, I. et al. (2000) "Spared Nerve Injury: An Animal Model of Persistent Peripheral Neuropathic Pain" Pain. 87:149-158.

Definition of derivative and analog from <http://cancerweb.ncl.ac.uk/omd/about.html>, pp. 1-5. Accessed Jul. 7, 2005.

Dellwo, A. (2009) "Definition of: Allodynia" About.com: Fibromyalgia & Chronic Fatigue. 1.

Dirksen, R.T. et al. (2004) "Distinct Effects on Ca2+ Handling Caused by Malignant Hyperthermia and Central Core Disease Mutations in RyR1" Biophysical Journal. 87(5):3193-3204.

Doty, P. et al. (2004) "Update on the Clinical Development of SPM 927 (formerly harkoseride)" Presented at EILAT VII, May 2004. Schwarz Biosciences. 1-25.

Doty, P. et al. (2004) in Bialer, M. et al. (2004) "Progress Report on New Antiepileptic Drugs: A Summary of the Seventh Eilat Conference (EILAT VII)" Epilepsy Research. 61:14-16.

Dowdall, T. et al. (2005) "Comparison of Five Different Rat Models of Peripheral Nerve Injury" Pharmacology, Biochemistry and Behavior. 80:93-108.

Dubuisson D. et al. (1977) "The Formalin Test: A Quantitative Study of the Analgesic Effects of Morphine, Meperidine, and Brain Stem Stimulation in Rats and Cats" Pain. 4:161-174.

Duncan G.E. et al. (2005)"The Novel Antiepileptic Drug Lacosamide Blocks Behavioral and Brain Metabolic Manifestations of Seizure Activity in the 6 Hz Psychomotor Seizure Model" Epilepsy Research. <javascript:AL_get(this,%20'jour',%20'Epilepsy%20Res.');> 67(1-2):81-7.

Dunham, N.W. et al. (1957) "A note on a simple apparatus for detecting neurological deficit in rats and mice" Journal of the American Pharmaceutical Association. 46(3):208-209.

Eller, J.L. et al. (2005) "Trigeminal neuralgia: definition and classification" Neurosurg. Focus. 18(5):E3.

Elliott, J.R. (1997) "Slow Na+ channel inactivation and bursting discharge in a simple model axon: implications for neuropathis pain" Brain Research. 754:221-226.

Erichsen, H.K. et al. (2002) "Pharmacological characterization of the spared nerve injury model of neuropathic pain" Pain. 98:151-161.

Errington, A.C. et al. (2005) "Lacosamide has a unique molecular mode of action" Poster presented at AES Scientific Exhibit, Dec. 2-5, 2005. Schwarz Biosciences. 1.

Errington, A.C. et al. (2006) "Seeking a mechanism of action for the novel anticonvulsant lacosamide" Neuropharmacology. 50(8):1016-1029. (PubMed Abstract Only).

European Search Report for Application No. 10185770.4—2123 dated Mar. 4, 2011.

Eustice, C. et al. (2009) "Fibromyalgia—Test Your Knowledge" About.com: Rheumatoid Arthritis / Joint Conditions. 1-4.

Everill, B. et al. (2001) "Sodium Currents of Large (AB-Type) adult cutaneous afferent dorsal root ganglion neurons display rapid recovery from inactivation before and after axotomy" Neuroscience. 106(1):161-169.

Field, M.J. et al. (1997) "Gabapentin (neurontin) and S-(+)-3-isobutylgaba represent a novel class of selective antihyperalgesic agents" British Jousnal of Pharmacology, 121:1513-1522.

Field, M.J. et al. (2002) "Gabapentin and the neurokinin1 receptor antagonist Cl-1021 act synergistically in two rat models of neuropathic pain" Journal of Pharmacology and Experimental Therapeutics, 303(2):730-735.

(56) References Cited

OTHER PUBLICATIONS

Fisher, A. et al. (2003) "Trigeminal Neuralgia: current treatments and future developments" Expert Opinion on Emerging Drugs, 8(1):123-143.

Fountain, N. B. et al. (2000) "Harkoseride: safety and tolerability of a new antiepileptic drug (AED) in patients with refractory partial seizures" Epilepsia, 41(Suppl. 7):169 (presentation attached).

Fountain, N. B. et al. (2003) "Absence of Effect of Adjunctive SPM 927 on Concomitant AED Plasma Concentrations in Subjects with Partial Seizures" Epilepsia, 44(Suppl. 9):96, abst. 1.269 (poster attached).

Freynhagen, R. et al. (2005) "Efficacy of pregabalin in neuropathic pain evaluated in a 12-week, randomised, double-blind, multicentre, placebo-controlled trial of flexible- and fixed-dose regiments" Pain, 115:254-263.

Gilron, I. et al. (2009) "A randomized, double-blind, controlled trial of perioperative administration of gabapentin, meloxicam and their combination for spontaneous and movement-evoked pain after ambulatory laparoscopic cholecystectomy" Pain Medicine, 108(2):623-630.

Gilron, I. et al., (2005) "Morphine, Gabaoentine or Their combination for neuropathic pain" New Englan Journal of Medicine, 352, 1324-1334.

Gilron, I., et al., (2005), "Combination pharmacotherapy for neuropathic pain: current evidence and future directions", Expert Rev. Neurotherapeutics, 5(6), 823-830.

Goldenberg, D.L. et al. (2004) "Management of Fibromyalgia Syndrome" Journal of Americal Medical Association, 292(19):2388-2395.

Gordon, R. et al. (1993) "Interaction of Felbamate with several other antiepileptic drugs against seizures induced by maximal electroshock in mice" Epilepsia 34(2):367-371.

Gower, A.J. et al. (1992) "Ucb L059, a novel anticonvulsant drug: pharmacological profile in animals." European Journal Pharmacology, 222(2-3):193-203; Erratum published in: European Journal Pharmacology (1993) 230:389 (PubMed Abstract Only).

Graven-Noelsen, T. et al. (1999) "Central hyperexcitability on fibromyalgia" Journal of Musculoskeletal Pain. 7: 261-271.

Grippo, A.J. et al. (2005) "Chronic mild stress induces behavioral and physiological changes, and may alter serotonin 1A receptor function, in male and cycling female rats" Psychopharmacology, 179:769-780.

Gur, A. et al. (2002) "Cytokines and depression in cases with fibromyalgia." Journal of Rheumatology, 29: 358-361.

Guzman, R.E. et al. (2003) "Mono-iodoacetate-induced histologic changes in subchondral bone and articular cartilage of rat femorotibial joints: An animal model of osteoarthritis" Toxicologic Pathology, 31(6): 619-624.

Hama, A.T. et al. (1999) "NMDA-induced spinal hypersensitivity is reduced by naturally derived peptide analog [Ser1] histogram" Pharmacological Biochemistry and Behavior, 62:67-74.

Han, H.C. et al. (2000) "Characteristics of ectopic discharges in a rat neuropathic pain model" Pain, 84:253-261.

Hao, J.X. et al. (2004) "SPM 927, a new anti-epileptic drug, alleviates neuropathic pain-like behaviors in rats after spinal cord or trigeminal nerve injury" Poster presented at Neuropathic Pain—Changing Paradigms in Diagnosis and Treatment, Madrid, May 2004.

Heers, C. et al. (2006) "The preclinical profile of the novel anticonvulsant lacosamide" Poster presented at European Congress on Epileptology 2006.

Henriksson, K.G. (1999) "Is fibromyalgia a distinct clinical entity? Pain mechanisms in fibromyalgia syndrom: a myologist's view" Baillière's Clinical Rheumatology, 13(3):455-461.

Heppelman, B. (1997) "Anatomy and histology of joint innervation" Journal of the Peripheral Nervous System, 2(1): 5-1.

Hidvegi,T. et al. (2006) "Lacosamide in subjects with painful distal diabetic neuropathy: results of a multi-center, open-label, follow-on trial" Poster presented at American Pain Society, May 3-6, 2006.

Hofmann, H.A. et al. (2003) "Pharmacological sensitivity and gene expression analysis of the tibial nerve injury model of neuropathic pain" European Journal of Pharmacology 470:17-25.

Holmberg, P. et al. (2004) "Novel 2-aminotitralin and 3-aminochroman derivatives as selective serotonin 5-HT7 receptor agonists and antagonists" Journal of Medicinal Chemistry, 47:3927-3930.

Hong, S. et al. (2004) "Early painful diabetic neuropathy is associated with differential changes in tetrodotoxin-sensitive and -resistant sodium channels in dorsal root ganglion neutons in the rat" Journal of Biological Chemistry, 279(28):29341-29350.

Honore, P. et al. (2000) "Murine models of inflammatory, neuropathic and cancer pain each generates a unique set of neurochemical changes in the spinal cord and sensory neurons" Neuroscience, 98(3):585-598.

Horstmann, R. et al. (2002) "Basic clinical pharmacological investigations of the new antiepileptic drug SPM 927" Epilepsia, 43(Suppl. 7):188, abst. 2.174 (poster attached).

Horstmann, R. et al. (2003) "SPM 927 does not interact with valproic acid and carbamazepine" Epilepsia, 44(Suppl. 9):97, Abst. 1.271 (poster attached).

Horstmann, R. et al. (2003) "SPM 927 does not prolong the QTc interval" Poster presented at 6th International Conference on the Mechanisms and Treatment of Neuropathic Pain, San Francisco, Sep. 18-20, 2003.

Hovinga, C.A. (2002) "Novel anticonvulsant medications in development" Expert Opin. Investig. Drugs, 11(10) 1387-1406.

Hovinga, C.A. (2003) "Erlosamide: Schwarz Pharma" !IDrugs, 6(5):479-485.

http://www.arthritis.org/key-messages.php> (Feb. 28, 2011).

http://www.everydayhealth.com/epilepsy/preventing-epilepsy-seizures.aspx Accessed Aug. 2, 2011.

http://www.ninds.nih.gov/disorders/epilepsy/detail_epilepsy.htm Accessed Aug. 2, 2011.

Hunskaar, S. et al. (1985) "Formalin test in mice, a useful technique for evaluating mild analgesics" Journal of Neuroscience Methods, 14:69-76.

Hunt, A. (2003) "Musculoskeletal fitness: the keystone in overall well-being and injury prevention" Clinical Orthopaedics and Related Research, 409, 96-105.

Hurley, R.W. et al. (2002) "Gabapentin and pregabalin can interact synergistically with naproxen to produce antihyperalgesia" Anesthesiology, 97:1263-1273.

Ilyin, V.I. et al. (2005) "V102862 (Co 102862): a potnet, broad-spectrum state-dependent blocker of mammalian voltage-gated sodium channels" British Journal of Pharmacology, 144:801-812.

International Search Report for WO/2007/020103 dated Mar. 1, 2007.

International Preliminary Report on Patentability for Application No. PCT/EP2007/005304 dated Dec. 16, 2008.

Iyenger, S. et al. (2004) "Effucacy of duloxetine, a potent and balanced serotonin-norepinephrine reuptake inhibitor in persistent pain models in rats" Journal of Pharmacolgy and Experimental Therapeutics, 311 (2), 576-584.

Jain, K.K. (2000) "A guide to drug evaluation for chronic pain" Emerging Drugs, 5(2):241-257.

Jensen, T.S. (2000) "Assessment and treatment of neuropathic pain" European Journal of Neurology, 7(Suppl. 3):3-4, abst. MT-9.

Kalbhen, D.A. (1987) "Chemical model of osteoarthritis—a pharmacological evaluation." Journal of Rheumatology, 14 Spec No: 130-131.

Kalso, E. (2005) "Sodium channel blokers in neuropathic pain" Current Pharmaceutical Design, 11:3005-3011.

Kemp, J.A. et al. (2002) "NMDA receptor pathways as drug targets" Nature Neuroscience Supplement, 5:1039-1042.

Kenney, P. et al. (2006) "A multi-center, randomized, double-blind, placebo-controlled trial to assess the efficacy and safety of lacosamide (200, 400, and 600mg/day) in subjects with painful distal diabetic neuropathy" Poster #774 presented at the American Pain Society Annual Meeting 2006.

Kerry, D.W. et al. (1975) "Trimethoprim and rifampicin: in vitro activities separately and in combination." Journal of Antimicrobial Chemotheraphy, 1:417-427.

Kim, S.H. et al. (1992) "An experimental model for peripheral neuropathy produced by segmental spinal nerve ligation in the rat" Pain, 50(3):355-363.

(56) References Cited

OTHER PUBLICATIONS

Klitgaard, H. et al. (1998) "Evidence for a unique profile of levetiracetam in rodent models of seizures and epilepsy" European Journal of Pharmacology, 353(2-3):191-206 (PubMed Abstract Only).
Kniffki, K.D. et al. (1978) "Responses of group IV afferent units from skeletal muscle to stretch, contraction and chemical stimulation" Experimental Brain Research, 31:511-522.
Knowles, E.A. et al. (2002) "Painful diabetic neuropathy: assessment and treatment." Journal of Diabetes Nursing, Jul./Aug. 2002.
Kohn, H. et al. (1988) "Marked stereospecificity in a new class of anticonvulsants" Brain Research, 457:371-375.
Kramer, G. (1997) "The limitations of antiepileptic drug monotherapy" Epilepsia, 38 (Suppl. 5):S9-S13.
Kropeit, D. et al. (2004) "Bioequivelance of short-time infusions compared to oral administration of SPM 927" Epilepsia, 45(Suppl. 7): 123, abst. 1.323 (poster attached).
Kropeit, D. et al. (2005) "Low drug-interaction potential of Lacosamide" Poster 702 presented at American Pain Society 2005 (abstract at http://www.ampainsoc.org/db2/abstract/view?poster_id=2394#702).
Kropeit, D. et al. (2006) "Lacosamide has low potential for drug-drug-interaction" Poster 851 presented at American Pain Society 2006.
Laguna Medical Systems (1999) <http://www.lagunamedsys.com/edgearchive/feature011599.htm> [retrieved Nov. 10, 2010].
Lai, J. et al. (2003) "The role of voltage-gated sodium channels in neuropathic pain" Current Opinion in Neurobiology, 13:291-297.
Lai, J. et al. (2004) "Voltage-gated sodium channels and hypperalgesia" Annual Review of Pharmacology and Toxicology, 44:371-397.
Lampert, A. et al. (2006) "Upregulation of persistent and ramp sodium current in dorsal horn neurons after spinal cord injury" Experimental Brain Research, 174(4):660-666.
Landsberg, P.G. et al. (2003) "Evaluation of cyclooxygenase 2 inhibitor use in patients admitted to a large teaching hospital" Internal Medicine Journal, 33: 225-228.
Larson, A.A. et. al. (2001) "Nociceptive Aspects of Fibromyalgia" Current Pain and Headache Reports, 5: 338-346.
Lawand, N. B. et al. (1997) "Excitatory amino acid receptor involvement in peripheral nociceptive transmission in rats" European Journal of Pharmacology, 324:169-177.
Lee, B.H. et al. (2000) "An animal model of neuropathic pain employing injury to the sciatic nerve branches" NeuroReport, 11(4):657-661.
Lee, S. et al. (2002) "Collapsin response mediator protein-2 inhibis neuronal phospholipase D2 activity by direct interaction" Journal of Biological Chemistry, 277(8):6542-6549.
Lesser, H. et al. (2004) "Pregabalin relieves symptoms of painful diabetic neuropathy" Neurology, 63:2104-2110.
LeTiran, A. et al. (2002) "Design and evaluation of affinity labels of functionalized amino acid anticonvulsants" Journal of Medicinal Chemistry, 45:4762-4773.
Litchfield, J.T. et al. (1949) "A simplified method of evaluating dose-effect experiments" Journal of Pharmacology and Experimental Therapeutics, 96:99-113.
Llewelyn, J.G. (2003) "Diabetic neuropathies: Types, diagnosis and management" Journal of Neurol Neurosurg Psychiatry, 74:ii15-ii9.
Lockwood, A.H. et al. (2002) "Tinnitus" N Engl J Med, 347(12):904-910.
Loiseau, P. et al. (1988) "Do we need novel anti-epileptic drugs?" British Journal of Clinical Practice, 42:2-3.
Lu, Y. et al. (1999) "Gabapentin attenuates nociceptive behaviors in an acute arthritis model in rats" The Journal of Pharmacology and Experimental Therapeutics, 290:214-219.
Luszczki, J.J. et al. (2003) "Interactions between oxcarbazepine and conventional antiepileptic drugs in the maximal electroshock test in mice: an isobolographic analysis" Epilepsia, 44(4):489-499 (PubMed Abstract Only).

Luszczki, J.J. et al. (2003) "Interactions of lamotrigine with topiramate and first-generation antiepileptic drugs in the maximal electroshock test in mice: an isobolographic analysis" Epilepsia, 44(8):1003-1013 (PubMed Abstract Only).
Luszczki, J.J. et al. (2003) "Isobolographic and subthreshold methods in the detection of interactions between oxcarbazepine and conventional antiepileptics—a comparative study" Epilepsy Research, 56(1):27-42 (PubMed Abstract Only).
Luszczki, J.J. et al. (2006) "Pharmacodynamic and pharmacokinetic characterization of interactions between Levetiracetam and numerous antiepileptic drugs in the mouse maximal electroshock seizure model: an isobolographical analysis" Epilepsia, 47(1):10-20.
Lynch, J.J. et al. (2004) "Attenuation of mechanical allodynia by clinically utilized drugs in a rat chemotherapy-induced neuropathis pain model" Pain, 110:56-63.
Löscher, W. et al. (1991) "The role of technical, biological and pharmacological factors in the laboratory evaluation of anticonvulsant drugs. IV. Protective indices" Epilepsy Research, 9(1):1-10 (PubMed Abstract Only).
Löscher, W. et al. (1993) "Profile of ucb L059, a novel anticonvulsant drug, in models of partial and generalized epilepsy in mice and rats" European Journal of Pharmacology, 232(2-3):147-158 (PubMed Abstract Only).
Mach, D.B. et al. (2002) "Origins of skeletal pain: sensory and sympathetic innervation of the mouse femur" Neuroscience, 113(1):155-166.
Macres, S.M. (2000) "Understanding neuropathic pain" Found at: www.spineuniverse.com/displayarticle.php/article1614. html <http://www.spineuniverse.com/displayarticle.php/article1614.%20html>.
Maier, C. et al. (2004) "A pilot randomized, double-blind, placebo-controlled pilot trial to investigate safety and efficacy of SPM 927 in subjects with postherpetic neuralgia" Poster presented at Neuropathic Pain, May 13-14, 2004.
Majumdar, S. et al. (2004) "Induction of pseudo-periodic oscillation in voltage-gated sodium channel properties is dependent on the duration of prolonged depolarization" European Journal of Neuroscience, 20:127-143.
March, J. (1985) Advanced Organic Chemistry: Reactions, Mechanisms, and Structure. New York: Wiley, pp. 16-18.
Matthews, E. A. et al., (2002) "A combination of gabapentin and morphine mediates enhanced inhibitory effects on dorsal horn neuronal respones in a rat model of neuropathy" Anesthesiology, 96:633-40.
Mayo Clinic, "Phantom Pain" <http://www.mayoclinic.com/health/phantom-pain/DS00444/DSECTION=causes> [retrieved on Jul. 9, 2009].
McCain, G.A. (1994) in Wall & Melzack, eds., "Fibromyalgia and myofascial pain". Textbook of Pain. Churchill Livingstone, New York, pp. 475-493.
McCleane, G. (2003) "Pharmacological management of neuropathic pain" CNS Drugs, 17(14):1031-1043.
McCleane, G. et al. (2003) "Does SPM 927 have an analgesic effect in human neuropathis pain? An open label study" Neuroscience Letters, 352:117-120.
McGivern, J.G. et. al. (2004) "Voltage-gated calcium channels as targets for the treatment of chronic pain" Curr. Drug Targets. CNS and Neuro. Disorders, 3(6) 457-478 (PubMed Abstract Only).
Mease, P. (2005) "Fibromyalgia syndrome: review of clinical presentation, pathogenesis, outcome measures, and treatment" The Journal of Rheumatology, 32: 6-21.
Meinardi, H. (1995) in Levy et al. "Use of Combined Antiepileptic Drug Therapy" Antiepileptic Drugs, 4th ed., chap. 6:91-97; Raven Press, Ltd., New York.
Mense, S. et al. (1991) "Discharge behaviour of feline gamma-motoneurones following induction of an artificial myositis" Pain, 46:201-210.
Mohapatra, D.P. et al. (2003) "A tyrosine residue in TM6 of the vanilloid receptor TRPV1 involved in desensitization and calcium permeability of capsaicin-activated currents" Molecular and Cellular Neuroscience, 23:314-324.

(56) References Cited

OTHER PUBLICATIONS

Moller, A.R. (2000) "Similarities between severe tinnitus and chronic pain" Journal of the American Academy of Audiology, 11(3):115-124.
Morrow, T.J. et al. (2001) "Antinociceptive properties of the anticonvulsant SPM927 (harkoseride) in rat" Soc. Neurosci. Conf. Abst. 508.16.
Morrow, T.J. et al. (2003) "The effects of lacosamide in animal models for acute, inflammatory and neuropathic pain" Poster presented at AES Scientific Exhibit, Dec. 5-10, 2003.
Nakata, K. et al. (2003) "The human dihydropyrimidinase-related protein 2 gene on chromosome 8p21 is associated with paranoid-type schizophrenia" Society of Biological Psychiatry, 53:571-576.
Nampiaparampil, D.E. et al. (2004) "Clinical: A review of Fibromyalgia". American Journal of Managed Care, 10(11 Pt 1): 794-800.
Nordenskiold, U.M. et al. (1993) "Grip force in patients with Rheumatoid Arthritis and Fibromyalgia and in healthy subjects. A study with Grippit Instrument" Scand. Journal of Rheumatolalgy, 22:14-19.
Office Action dated Feb. 11, 2004 issued in U.S. Appl. No. 10/344,885.
Office Action dated Jun. 13, 2006 issued in U.S. Appl. No. 11/089,441.
Office Action dated Sep. 11, 2006 issued in U.S. Appl. No. 11/149,181.
Office Action dated Sep. 21, 2006 issued in U.S. Appl. No. 11/145,965.
Office Action dated Sep. 27, 2006 issued in U.S. Appl. No. 10/466,295.
Office Action dated Oct. 2, 2006 issued in U.S. Appl. No. 11/148,429.
Office Action dated Nov. 28, 2006 issued in U.S. Appl. No. 11/002,414.
Office Action dated Dec. 27, 2006 issued in U.S. Appl. No. 11/342,140.
Office Action dated Dec. 28, 2006 issued in U.S. Appl. No. 11/089,441.
Office Action dated Feb. 5, 2007 issued in U.S. Appl. No. 11/149,181.
Office Action dated Aug. 8, 2007 issued in U.S. Appl. No. 10/466,295.
Office Action dated Sep. 11, 2007 issued in U.S. Appl. No. 11/507,110.
Office Action dated Oct. 29, 2007 issued in U.S. Appl. No. 11/342,140.
Office Action dated Dec. 7, 2007 issued in U.S. Appl. No. 11/148,429.
Office Action dated Dec. 27, 2007 issued in U.S. Appl. No. 11/506,523.
Office Action dated Dec. 27, 2007 issued in U.S. Appl. No. 11/506,578.
Office Action dated May 29, 2008 issued in U.S. Appl. No. 11/145,965.
Office Action dated Jun. 4, 2008 issued in U.S. Appl. No. 10/466,295.
Office Action dated Jul. 10, 2008 issued in U.S. Appl. No. 11/507,110.
Office Action dated Jul. 28, 2008 issued in U.S. Appl. No. 11/148,429.
Office Action dated Aug. 20, 2008 issued in U.S. Appl. No. 11/342,140.
Office Action dated Oct. 6, 2008 issued in U.S. Appl. No. 11/506,523.
Office Action dated Oct. 6, 2008 issued in U.S. Appl. No. 11/506,578.
Office Action dated Oct. 29, 2008 issued in U.S. Appl. No. 11/506,577.
Office Action dated Jan. 22, 2009 issued in U.S. Appl. No. 11/000,951.
Office Action dated Feb. 19, 2009 issued in U.S. Appl. No. 10/466,295.
Office Action dated Mar. 31, 2009 issued in U.S. Appl. No. 11/342,140.
Office Action dated Apr. 17, 2009 issued in U.S. Appl. No. 11/507,110.
Office Action dated Apr. 29, 2009 issued in U.S. Appl. No. 11/506,578.
Office Action dated May 12, 2009 issued in U.S. Appl. No. 11/506,577.
Office Action dated Jun. 23, 2009 issued in U.S. Appl. No. 11/506,524.
Office Action dated Jul. 22, 2009 issued in U.S. Appl. No. 11/506,523.
Office Action dated Jul. 22, 2009 issued in U.S. Appl. No. 10/466,295.
Office Action dated Oct. 21, 2009 issued in U.S. Appl. No. 11/342,140.
Office Action dated Dec. 17, 2009 issued in U.S. Appl. No. 11/148,429.
Office Action dated Dec. 17, 2009 issued in U.S. Appl. No. 11/506,577.
Office Action dated Feb. 3, 2010 issued in U.S. Appl. No. 11/506,524.
Office Action dated Feb. 3, 2010 issued in U.S. Appl. No. 11/507,110.
Office Action dated Mar. 17, 2010 issued in U.S. Appl. No. 10/466,295.
Office Action dated Apr. 9, 2010 issued in U.S. Appl. No. 11/506,523.
Office Action dated Apr. 15, 2010 issued in U.S. Appl. No. 12/188,419.
Office Action dated Aug. 2, 2010 issued in U.S. Appl. No. 11/506,524.
Office Action dated Aug. 19, 2010 issued in U.S. Appl. No. 11/507,110.
Office Action dated Nov. 15, 2010 issued in U.S. Appl. No. 11/506,523.
Office Action dated Nov. 15, 2010 issued in U.S. Appl. No. 12/063,956.
Office Action dated Jan. 14, 2011 issued in U.S. Appl. No. 12/304,023.
Office Action dated Mar. 17, 2011 issued in U.S. Appl. No. 12/063,956.
Office Action dated Mar. 28, 2011 issued in U.S. Appl. No. 11/506,524.
Office Action dated Apr. 7, 2011 issued in U.S. Appl. No. 12/304,023.
Office Action, dated Oct. 18, 2011 issued in U.S. Appl. No. 11/506,524.
Office Action dated Jan. 10, 2012 issued in U.S. Appl. No. 12/304,023.
Office Action dated Jul. 17, 2012 issued in U.S. Appl. No. 12/304,012.
Office Action dated Jul. 20, 2012 issued in U.S. Appl. No. 13/428,419.
Office Action dated Sep. 11, 2012 issued in U.S. Appl. No. 12/304,012.
Office Action dated Dec. 12, 2012 issued in U.S. Appl. No. 13/428,419.
Office Action dated Aug. 15, 2012 issued in U.S. Appl. No. 13/442,212.
Office Action dated Jan. 7, 2013 issued in U.S. Appl. No. 13/442,212.
Office Action dated Mar. 22, 2013 issued in U.S. Appl. No. 12/306,953.
Office Action dated May 15, 2013 issued in U.S. Appl. No. 13/428,419.
Office Action dated May 20, 2013 issued in U.S. Appl. No. 13/442,212.
Office Action dated Sep. 9, 2013 issued in U.S. Appl. No. 12/304,023.
Papapetropoulos, S. et al. (2007) "Botulinum toxin in movement disorders" Seminars in Neurology, 27(2):183-194.
Patel, D. et al. (2001) "The effects of GABAB agonists and gabapentin on mechanical hyperalgesia in models of neuropathic and inflammatory pain in the rat" Pain, 90:217-226.
Patsalos, P.N. (2000) "Pharmacokinetic profile of levetiracetam: toward ideal characteristics" *Pharmacology and Therapeutics*, 85:77-85.
Patsalos, P.N. (2004) "Levetiracetam: pharmacology and therapeutics in the treatment of epilepsy and other neurological condications" Review of Contemporary Pharmacother., 13:1-168.

(56) References Cited

OTHER PUBLICATIONS

Perkins, B.A. et al. (2002) "Diagnosis and management of diabetic neuropathy" Current Diabetes Reports, 2:495-500.

Pessoa-Mahana, H. et al. (2003) "A synthetic overview of new molecules with 5-HT1A binding affinities" Mini Review of Medicinal Chemistry, 3:77-93.

Pollard, J. et al. (2006), "Antiepileptic drugs in development", Lancet Neurology, 5: 1064-1067.

Poncelet, A.N. (2003) "Diabetic polyneuropathy. Risk factors, patterns of presentation, diagnosis, and treatment" Geriatrics, 58(6) 16-30.

Pongratz, D.E. et al. (1998) "Morphologic aspects of fibromyalgia" Z. Rheumatology, 57(Suppl. 2):47-51.

Porreca, F. et al. (1990) "Modulation of morphine antinociception by peripheral [Leu5]enkephalin: a synergistic interaction" European Journal of Pharmacology, 179(3):463-468 1067 (PubMed Abstract Only).

Priestley, T. (2004) "Voltage-gated sodium channels and pain" Current Drug Targets—CNS & Neurological Disorders, 3:441-456.

Raja, S.N. et al. (2005) "Combination therapy for neuropathic pain—which durgs, which combination, which patients?" N Eng J Med, 352(13):1373-1375.

Randall, L.O. et al. (1957) "A method for measurement of analgesic activity on inflamed tissue" Arch. Int. Pharmacodyn., 91:409-419.

Rauck, R. et al. (2003) "A randomized, double-blind, placebo-controlled trial to investigate the safety and efficacy of SPM 927 in painful diabetic neuropathy" Poster presented at 6th Int. Conf. on Mechanisms and Treatment of Neuropathic Pain, Sep. 2003.

Rauck, R.L. et al. (2007) "Lacosamide in painful diabetic peripheral neuropathy. A phase 2 double-blind placebo-controlled study" Clinical Journal of Pain, 23(2):150-158.

Rauschkolb, C. et al. (2004) "SPM 927, a novel promising pain treatment" Presented at Visiongain Pain Management, 2004.

Remy, C. et al. (2004) "Modulation of voltage-dependent sodium channels by the d-agonist SNC80 in acutely isolated rat hippocampal neurons" Neuropharmacology, 47:1102-1112.

Reynolds, E.H. et al. (1981) "Single Drug or combination therapy of epilepsy?" Drugs, ADIS Int'l Ltd., 21:374-382.

Richeimer (2000) "The Richeimer Pain Update: Understanding nociceptive and neuropathic pain" http:/www.helpforpain.com/arch2000dec.htm.

Rodger, W. (1991) "Non-insulin dependent (type II) diabetes mellitus" Canadian Medical Association Journal, 145:1571-1581.

Rogawski, M. et al. (2006) "Diverse mechanisms of antiepileptic drugs in the development pipeline" Epilepsy Research, 69: 273-294.

Rosenfeld, W. et al. (2003) "Long-term safety and efficacy of SPM 927 as adjunctive therapy in subjects with partial seizures: 24 week follow-up" Epilepsia, 44(Suppl. 9):262, abst. 2.249 (poster attached).

Rosenfeld, W. et al. (2005) "Pharmacokinetics and safety of intravenous lacosamide administered as replacement for adjunctive oral lacosamide in patients with partial-onset seizures" Epilepsia, 46(Suppl. 8):184, abst. 2.278 (poster attached).

Rosenstock, J. et al. (2004) "Pregabalin for the treatment of painful diabetic peripheral neuropathy: a double0blind, placebo-controlled trial" Pain, 110:628-638.

Rush, A.M. et al. (2006) "A single sodium channel mutation produces hyper-or hypoexcitability in different types of neurons" Proceedings of the National Academy of Science of the U.S.A., 103(21):8245-8250.

Rüttiger, L. et al. (2003) "A behavioral paradigm to judge acute sodium salicylate-induced sound experience in rats: a new approach for an animal model ion tinnitus" Hearing Research, 180:39-50.

Sachdeo, R. et al. (2003) "An open-label, maximum tolerated dose trial to evaluate oral SPM 927 as adjunctive therapy in patients with partial seizures" Poster presented at 55th Annual Meeting, American Academy of Neurology, Mar. 2003.

Saddi, G.M. et al. (2000) "The formalin test in the mouse: a parametric analysis of scoring properties" Pain, 89:53-63.

Sander, J.W.A.S. et al. (1987) "Incidence and prevalence studies in epilepsy and their methodological problems: a review" Journal of Neurology Neurosurgery Phychiatry, 50:829-839.

Schaible, H.G. et al. (2002) "Mechanisms of pain in arthiritis" Annual New York Academy of Sciences, 966: 343-354.

Schernthaner, G. (1996) "Cardiovascular mortality and morbidity in type-2 diabetes mellitus" Diabetes Resarch and Clinical Practice, 31:S3-S13.

Schiltmeyer, B. et al. (2004) "Pharmacokinetics of the new antiepileptic drug SPM 927 in human subjects with different age and gender" Epilepsia, 45(Suppl. 7):313, abst. 2.361 (poster attached).

Schiltmeyer, B. et al. (2006) "No interaction between lacosamide and metformin" Poster 850 presented at American Pain Society 2006 (abstract at <http://www.ampainsoc.org/db2/abstract/view?poster_id=2847> #850).

Schäfers, M. et al. (2003) "Intramuscular injection of tumor necrosis factor-alpha induces muscle hyperalgesia in rats" Pain, 104(3):579-588.

Schürcks, M. et. al. (2008) "Migraine, allodynia, and implications for treatment" European Journal of Neurology, 15 : 1279-1285.

Seizure Disorders from Merck manual, pp. 1-13. Accessed Apr. 1, 2011.

Seltzer, Z. et al. (2001) "Mapping a gene for neuropathic pain-related behavior following peripheral neurectomy in the mouse" Pain, 93:101-106.

Shaibani, A. et al. (2005) "An open-label follow-on trial to assess the long-term safety and efficacy of oral lacosamide in subjects with diabetic neuropathy" Poster presented at World Congress on Pain, Aug. 21-26, 2005.

Shiro, Y. et al. (1996) "Effect of chronic ipsapirone treatment on the density of 5-HT1A receptors and 5-HT1A receptor in mRNA in discrete regions of the rat brain" Psychiatry Clinical Neurosciences, 50:141-146.

Silver, K. et al. (2005) "State-dependent block of rat Nav 1.4 sodium channels expressed in *Xenopus* oocytes by pyrazoline-type insecticides" Neurotoxicology, 26:397-406.

Simmons, Z. et al. (2002) "Update on diabetic neuropathy" Current Opinion in Neurology, 15:595-603.

Sindrup, S.H. et al. (1999) "Efficacy of pharmacological treatments of neuropathic pain: an update and effect related to mechanism of drug action" Pain, 83:389-400.

Sommerville, K. et al. (2004) "Intravenous SPM 927 (formerly harkoseride)" Presented at EILAT VII, May 2004.

Sommerville, K.W. (2003) "Schwarz Pharma's Neurology Pipeline" Presentation found at: http://www.schwarzpharma.com/_uploads/assets/1369_4_neurology_KNS_<http://www.schwarzpharma.com/_uploads/%20assets/1369_4_neurology_KNS_>190203.pdf.

Stables, J.P. et al. (1997) in Avanzani et al. "The NIH anticonvulsant drug development (ADD) program: preclinical anticonvulsant screening project" Molecular and Cellular Targets for Antiepileptic Drugs, chap. 16, pp. 191-198; London: Libbey & Co., Ltd.

Staud, R. (2007) "Treatment of fibromyalgia and its symptoms" Expert Opinion, 8 (11) :1629-1642.

Staud, R. et al. (2001) "Abnormal sensitization and temporal summation of second pain (wind-up) in patients with fibromyalgia syndrome" Pain, 91:165-175.

Staud, R. et al. (2002) "Peripheral and central sensitization in fibromyalgia: pathogenitic role" Current Paind and Headache reports, 6: 259-266.

Stein, C. et al. (1988) "Unilateral inflammation of the hidpaw in rats as a model of prolonged noxious stimulation: alterations in behavior and nociceptive thresholds" Pharmacology Biochemistry and Behavior, 31:445-451.

Stoehr, T. et al. (2005) "Lacosamide displays potent antinociceptive effects in animal models for neuropathic and inflammatory pain" Poster presented at World Congress on Pain, Aug. 21-26, 2005.

Stoehr, T. et al. (2005) "The effect of lacosamide in comparison to other analgesics in rat models for neuropathic pain" Poster presented at 8th Int. Conf. on Mechanisms and Treatment of Neuropathic Pain, San Francisco, Nov. 3-5, 2005.

(56) References Cited

OTHER PUBLICATIONS

Stöhr, T. et al. (2006) "Lacosamide displays potent antinociceptive effects in animal models for inflammatory pain" European Journal of Pain,10:241-249.
Tahimic, C.G.T. et al. (2006) "Evidence for a role of collapsin response mediator protein-2 in signaling pathways that regulate the proliferation of non-neuronal cells" Biochemical and Biophysical Research Communications, 340:1244-1250.
Tallarida, R. (1992) "Statistical analysis of drug combinations for synergism" Pain, 49:93-97.
Tallarida, R.J. (2002) "The interaction index: a measure of drug synergism" Pain, 98(1-2):163-168 (PubMed Abstract Only).
Tallarida, R.J. et al. (1997) "Efficient designs or studying synergistic drug combinations" Life Sciences, 61:PL417-425 (PubMed Abstract Only).
Tallarida, R.J. et al. (1999) "Response surface analysis of synergism between morphine and clonidine" Journal of Pharmacology and Experimental Therapeutics, 289(1):8-13 (PubMed Abstract Only).
Tan, H.L. (2006) "Sodium channel variants in heart disease: expanding horizons" Journal of Cardiovascular Electrophysiology, 17(Suppl.1): S151-S157 (PubMed Abstract Only).
Teng, C.J. et al. (1998) "The formalin test: a dose-response analysis at three developmental stages" Pain, 76:337-347.
Thomas, et al. (1999) "Diabetic neuropathy: mechanisms and future options" Journal of Neurology Neurosurgery and Psychiatry, 67:277-279.
Tjølsen, A. et al. (1992) "The formalin test: an evaluation of the method" Pain, 51:5-17.
Tjølsen, A. et al. (1997) in Dickinson & Besson, ed., "The Pharmacology of Pain", chap. 1, pp. 1-20; Berlin: Springer-Verlag.
Vaiciene, N. et al. (2006) "Multicenter, open-label trial investigating safety and tolerability of intravenous lacosamide (SPM 927) as replacement for oral lacosamide in subjects with partial seizures: report of first cohort" Poster presented at European Congress on Epileptology 2006.
Vierck Jr., C.J. (2006) "Mechanisms underlying development of spatially distributed chronic pain (fibromyalgia)" Pain, 124: 242-263.
Vos, B.P. et al. (1994) "Behavioral evidence of trigeminal neuropathic pain following chronic constriction injury to the rat's infraorbital nerve" The Journal of Neuroscience, 14(5):2708-2723.
Warner, T. et al. (1992) Lamotrigine -induced carbamazepine toxicity: an interaction with carbamazepine-10,11-epoxide Epilepsy Research, 11(2):147-150 (PubMed Abstract Only).
Watson, G.S. et al. (1997) "Optimal scoring strategies and weights for the formalintest in rats" Pain, 70:53-58.
Wheeler-Aceto, H. et al. (1990) "The rat paw formalin test: comparison of noxious agents" Pain, 40:229-238.
Wheeler-Aceto, H. et al. (1991) "Standardization of the rat paw formalin test for the evaluation of analgesics" Psychopharmacology, 104:35-44.
Whitesides, J. et al. (2004) "Long-term safety and efficacy of lacosamide as adjunctive therapy in subjects with partial seizures: 48-week follow-up" Poster presented at AES Scientific Exhibit, Dec. 3-7, 2004.
Wieland, H., et al., (2005), "Osteoarthritis—an untreatable disease?", Nature Reviews Drug Discovery, 4: 331-344.
Wolfe, F. et al. (1990) "The American College of Rheumatology 1990 criteria for the classification of fibromyalgia: Report of the Multicenter Criteria Center" Arthritis and Rheumatism, 33:160-172.
Wood, J.N. et al. (2002) in "Sodium Channels and Neuronal Hyperexcitability", pp. 159-172; Chichester: Wiley.
Wood, J.N. et al. (2004) "Voltage-gated sodium channels and pain pathways" Journal of Neurobiology, 61:55-71.
Wu, F. et al. (2005) "A C-terminal skeleton muscle sodium channel mutation associated with myotonia disrupts fast inactivation" Journal of Physiology, 565.2:371-380.

www.cdc.gov/arthritis/data_statistics/arthritis_related_statistics. htm#2 <http://www.cdc.gov/arthritis/data_statistics/arthritis_related_statistics.htm> (printed Feb. 14, 2011).
www.cdc.gov/mmwr/preview/mmwrhtml/mm5318a3.htm <http://www.cdc.gov/mmwr/preview/mmwrhtml/mm5318a3.htm> (printed Feb. 14, 2011).
Wymer, J. et al. (2005) "A multi-center, randomized double-blind, placebo-controlled trial to assess the efficacy and safety of lacosamide in subjects with painful distal diabetic neuropathy" 8th Int. Conf. on Mechanisms and Treatment of Neuropathic Pain, San Francisco, Nov. 3-5, 2005.
Xu, X.J. et al. (1992) "Chronic ain-related syndrome in rats after ischemic spinal cord lesion: a possible animal model for pain in patients with spinal cord injury" Pain, 48(2):279-290 (abstract only).
Yezierski, R.P. et al. (1998) "Excitotoxic spinal cord injury: behavioral and morphological characteristic of a central pain model" Pain, 75:141-155.
Ziegler, D. et al. (2005) "Efficacy and safety of lacosamide in the treatment of neuropathic pain attributed to distal diabetic neuropathy" 8th Int. Conf. on Mechanisms and Treatment of Neuropathic Pain, San Francisco, Nov. 3-5, 2005.
Ben-Menachem, E. et al. Evidence for sustained efficacy of levetiracetam as add-on epilepsy therapy, *Epilepsy Research*, vol. 53, Issues 1-2, (2003) pp. 57-64.
Beren, R.G. et al. Efficacy and safety of levetiracetam 1000-3000mg/day in patients with refractory partial-onset seizures: a multicentre, open-label single-arm study, *Epilepsy Research*, vol. 63, No. 1, (2005) pp. 1-9.
Cereghino, J.J. et al. Levetiracetam for partical seizures results of a double-blind, randomized clinical trial, *Neurology*, vol. 55, No. 2, (2000) pp. 236-242.
Deckers, L.P. Place of polytherapy in early treatment of epilepsy, *CNS Drugs*, vol. 16, No. 3, (2002) pp. 155-163.
Kwan, P. et al. Combination Therapy in Epilepsy, *Drugs*, vol. 66, No. 14, (2006) pp. 1817-1829.
Oliveira, A.A. et al. Evaluation of levetiracetam effects on pilocarpine-induced seizures: cholinergic muscarinic system involvement, *Neuroscience Letters*, vol. 385, No. 3, (2005) pp. 185-188.
Prosser, H.M. et al. Epileptogenesis and enhanced prepulse inhibition in GABA-B1 deficient mice, *Molecular and Cellular Neurosciences*, vol. 17, (2001) pp. 1059-1070.
Brazil, C.W., et al. (2002) "Effects of levetiracetam on sleep in epilepsy patients", *Epilepsia*, 43(7):40.
Jatuzis, D., et al. (2005) "Evaluation of the effect of oral lacosamide on concomitant AED plasma concentrations in patients with partial seizures", *Epilepsia*, 46(8):170.
Barton, M.E., et al. "Pharmacological characterization of the 6 Hz psychomotor seizure model of partial epilepsy" (2001) *Epilepsy Research*, 47:217-227.
Bialer, M., et al. "Progress report on new antiepileptic drugs: a summary of the Seventh Eilat Conference (EILAT VII)" (2004) *Epilepsy Research*, 61:1-48.
Gutiérrez-Grobe, Y., et al. "Acute liver failure associated with levetiracetam and lacosamide combination treatment for unspecified epileptic disorder" (2013) *Case Reports in Emergency Medicine*, Article ID 634174.
Ben-Menachem, E. et al. (2005), "Efficacy and Safety of Adjunctive Oral Lacosamide for the Treatment of Partial Onset Seizures in Patients with Epilepsy", *Neurology*, 64(Suppl 1): 1 page, A187.
Bourgeois, B., et al. (1988), "Combined Administration of Carbamazepine and Phenobarbital: Effect on Anticonvulsant Activity and Neurotoxicity", *Epilepsia*, 29(4): 482-487.
Brigo, F., et al. (2013), "When one plus one makes three: The quest for rational antiepileptic polytherapy with supraadditive anticonvulsant efficacy", *Epilepsy & Behavior*, 27: 439-442.
de Biase, S., et al. (2014), "Lacosamide for the treatment of epilepsy", *Expert Opinion Drug Metab. Toxicol.*, 10(3): 1-10.
Snoeck, E. et al. (2004), "Dose-Response Population Analysis of Keppra(tm) Add-On Treatment in Epilepsy Patients with Partial Onset Seizures", *Epilepsia*, 45(Suppl. 7), 128-129.
Tallarida, R. (2001), "Drug Synergism: its Detection and Applications", *Perspectives in Pharmacology*, 298(3): 865-872.

| Drug | ED50 (mg/kg i.p.) |
|---|---|
| LCM | 10.1 (4.5 - 19.8) |
| LTG | 85.0 (48.0 - 145.2) |
| VPA | 132.0 (78.7 - 205.6) |
| CBZ | 48.1 (27.4 - 81.5) |
| PHT | 67.0 (39.6 - 111.6) |
| LEV | 22.8 (9.97 - 48.74) |
| TPM | 271,7 (143.0 - 493.0) |
| GBP | 224.0 (108.0 - 428.0) |

FIG. 9

| Drug combination | F | $ED_{50add}$ ± SEM | $ED_{50mix}$ ± SEM | ($\alpha$) |
|---|---|---|---|---|
| LTG + LCM | 1 : 3 | 28.8 ± 7.9 | 21.9 ±7.0 | 0.76 |
|  | 1 : 1 | 47.5 ±12.4 | 32.3 ±8.9 | 0.68 |
|  | 3 : 1 | 66.2 ± 17.0 | 24.7 ±8.6 | 0.37 |
| VPA + LCM | 1 : 3 | 40.5 ±9.7 | 35.4 ±13.1 | 0.87 |
|  | 1 : 1 | 71.0 ±16.1 | 53.7 ±19.3 | 0.76 |
|  | 3 : 1 | 101.5 ±22.4 | 79.6 ±22.5 | 0.78 |
| CBZ + LCM | 1 : 3 | 19.6 ±5.6 | 13.3 ±3.7 | 0.68 |
|  | 1 : 1 | 29.1 ±7.8 | 16.2 ±6.5 | 0.56 |
|  | 3 : 1 | 38.6 ±10.0 | 19.3 ±7.8 | 0.50 |
| PHT + LCM | 1 : 3 | 24.3 ±6.5 | 21.2 ±7.9 | 0.87 |
|  | 1 : 1 | 38.5 ±9.7 | 34.2 ±14.3 | 0.89 |
|  | 3 : 1 | 52.8 ±12.8 | 41.4 ±11.7 | 0.78 |
| LEV + LCM | 1 : 3 | 13.2 ±4.4 | 9.2 ±3.0 | 0.69 |
|  | 1 : 1 | 16.4 ±5.5 | 10.5 ±3.7 | 0.64 |
|  | 3 : 1 | 19.6 ±6.6 | 10.4 ±2.9 | 0.53 |
| TPM + LCM | 1 : 3 | 75.5 ±21.2 | 57.7 ±18.7 | 0.76 |
|  | 1 : 1 | 140.9 ±38.9 | 94.4 ±28.9 | 0.67 |
|  | 3 : 1 | 206.3 ±56.7 | 93.7 ±25.8 | 0.45 |
| GBP + LCM | 1 : 3 | 63.6 ±19.2 | 51.8 ±14.5 | 0.82 |
|  | 1 : 1 | 117.1 ±35.0 | 74.8 ±26.5 | 0.64 |
|  | 3 : 1 | 170.6 ±50.9 | 90.4 ±25.0 | 0.53 |

FIG. 10

| Treatment (mg/kg i.p.) | Mice impaired (%) |
|---|---|
| LCM (5.0) <br> LCM (10) | 0 <br> 20 |
| LTG (42.5) <br> LTG (85) <br> LCM (5.0) + LTG (42.5) | 40 <br> 95 <br> 50 |
| CBZ (24.0) <br> CBZ (48) <br> LCM (5.0) + CBZ (24.0) | 20 <br> 50 <br> 20 |
| VPA (66.0) <br> VPA (132) <br> LCM (5.0) + VPA (66.0) | 0 <br> 25 <br> 10 |
| PHT (33.0) <br> PHT (67) <br> LCM (5.0) + PHT (33.0) | 30 <br> 50 <br> 20 |
| LEV (11.4) <br> LEV (23) <br> LCM (5.0) + LEV (11.4) | 0 <br> 0 <br> 0 |
| TPM (133.9) <br> TPM (272) <br> LCM (5.0) + TPM (133.9) | 0 <br> 35 <br> 0 |
| GBP (112.0) <br> GBP (224) <br> LCM (5.0) + GBP (112.0) | 10 <br> 35 <br> 20 |

FIG. 11

| | 1 : 3 | 1 : 1 | 3 : 1 |
|---|---|---|---|
| LTG + LCM | synergism tendency | synergism | synergism |
| VPA + LCM | additivity | synergism tendency | synergism tendency |
| CBZ + LCM | synergism | synergism | synergism |
| PHT + LCM | additivity | additivity | synergism tendency |
| LEV + LCM | synergism | synergism | synergism |
| TPM + LCM | synergism tendency | synergism | synergism |
| GBP + LCM | additivity | synergism | synergism |

FIG. 12

| Species, Route | Test | Time of Test (hrs) | ED50 (mg/kg) | 95% C.I. | P.I.[a] |
|---|---|---|---|---|---|
| Mice, i.p. | Rotorod | .25 | 26.8[b] | 25.5-28.0 | — |
| | Frings AGS | .5 | 0.63 | 0.37-0.99 | 43[c] |
| | MES | .5 | 4.46 | 3.72-5.46 | 6.0 |
| | sc Met | .25 | >25 | | <1 |
| | sc Bic | 1 | >50 | | <0.5 |
| | sc Pic | 1 | >30 | | <0.9 |
| Rats, p.o. | MMI[d] | —[e] | >500[b] | | — |
| | MES | .5 | 3.90 | 2.58-6.20 | >128 |
| | sc Met | .5 | >250 | | |

[a] Protective Index = TD50/ED50
[b] Median toxic dose (TD50)
[c] P.I. calculated with TD50 obtained in CF#1 mice and ED50 in Frings mice
[d] Minimal motor impairment
[e] Tested at 1/4 through 24 hrs

FIG. 13

Profile of Anticonvulsant Activity and Minimal Toxicity of Prototype Anticonvulsants in Mice and Rats

| Substance | Mouse, i.p. TD50 or ED50 (mg/kg) and P.I.[a] | | | | | | Rat, p.o. TD50 or ED50 (mg/kg) and P.I.[a] | | |
|---|---|---|---|---|---|---|---|---|---|
| | TD50 | MES | sc Met | sc Bic | sc Pic | AGS | TD50 | MES | sc Met |
| valproic acid | 483 (412-571) | 287 (237-359) P.I. 1.7 | 209 (176-249) P.I. 2.3 | 437 (369-563) P.I. 1.1 | 311 (203-438) P.I. 1.5 | 155 (110-216) P.I. 3.1 | 859 (719-1148) | 395 (332-441) P.I. 2.2 | 620 (469-935) P.I. 1.4 |
| felbamate | 816 (590-1024) | 50.1 (35.8-61.7) P.I. 16 | 148 (121-171) P.I. 5.5 | >300 | 156 (122-202) P.I. 5.2 | 10.0 (8.19-12.0) P.I. 82 | >3000 | 47.8 (41.0-57.3) P.I. >63 | 238 (132-549) P.I. >13 |
| phenytoin | 42.8 (36.4-47.5) | 6.48 (5.65-7.24) P.I. 6.6 | >50 | >60 | >60 | 3.88 (2.67-5.50) P.I. 11 | >500 | 23.2 (21.4-25.4) P.I. >22 | >250 |
| lamotrigine | 48.0 (38.7-57.7) | 7.2 (6.1-8.45) P.I. 6.7 | >60 | >50 | >50 | 2.39 (1.62-3.38) P.I. 20 | 325 (259-419) | 3.21 (2.6-3.69) P.I. 101 | >250 |
| carbamazepine | 47.3 (39.2-59.2) | 9.85 (8.77-10.7) P.I. 4.9 | >50 | >60 | 28.9 (23.9-41.6) P.I. 1.7 | 11.2 (7.73-16.2) P.I. 4.3 | 381 (319-402) | 3.57 (2.41-4.72) P.I. 101 | >250 |
| gabapentin | >500 | 78.2 (46.6-127) P.I. >6.4 | 47.5 (17.9-86.2) P.I. >11 | >500 | >500 | 91.1 (61.8-129) P.I. >5.5 | 52.4 (35.2-76.2) | 9.13 (4.83-14.4) P.I. 6.7 | >100 |
| ethosuximide | 323 (279-379) | >350 | 128 (101-163) P.I. 2.5 | 365 (284-483) P.I. 0.9 | 211 (170-266) P.I. 1.53 | 328 (263-407) P.I. 1.0 | >500 | >250 | 204.2 (160-264) P.I. >2.5 |
| clonazepam | 0.27 (0.14-0.43) | 23.8 (16.4-31.7) P.I. 0.01 | 0.017 (0.012-0.025) P.I. 16 | 0.008 (0.005-0.012) P.I. 34 | 0.05 (0.03-0.07) P.I. 5.4 | 0.10 (0.09-0.11) P.I. 2.7 | 1.99 (1.71-2.32) | 2.41 (1.95-2.81) P.I. 0.8 | 0.77 (0.26-1.52) P.I. 2.6 |

( ) 95% confidence interval
[a] Protective Index = TD50/ED50

ANTICONVULSANT COMBINATION THERAPY

The present application is a continuation application of U.S. patent application Ser. No. 12/304,023, filed 9 Dec. 2008, which is a national stage application of International Patent Application No. PCT/EP2007/005304 filed on 15 Jun. 2007, which claims the priorities of U.S. provisional patent application Ser. No. 60/813,967 filed on 15 Jun. 2006, and of European patent applications EP 06 021 470.7 filed on 12 Oct. 2006, EP 06 021 469.9 filed on 12 Oct. 2006, and EP 06 024 241.9 filed on 22 Nov. 2006. Each of the above referenced patent applications is incorporated herein by reference in its entirety.

The present invention is directed to a pharmaceutical composition comprising a compound (a) of a class of peptide compounds and at least one further compound (b) for the prevention, alleviation or/and treatment of epileptic seizures wherein this composition has a synergistic effect on the prevention, alleviation or/and treatment of epileptic seizures as compared to the effect of the compounds (a) or (b) given alone.

Certain peptides are known to exhibit central nervous system (CNS) activity and are useful in the treatment of epilepsy and other CNS disorders. These peptides are described in the U.S. Pat. No. 5,378,729 and in U.S. Pat. No. 5,773,475, which are hereby incorporated by reference.

EP 1 541 138 is directed to the use of a class of peptide compounds for treating status epilepticus or related conditions, such as acute repetitive seizures and seizure clusters. EP 1 541 138 is further directed to the prevention of generalized tonic clonic convulsions.

Seizures are the consequence of a paroxysmal brain dysfunction related to excessive neuronal activity that leads to an alteration of behaviour or consciousness. Epilepsy represents the recurrence of two or more unprovoked seizures and represents a chronic brain disease.

There are two major types of seizures: partial or focal seizures, which originate in a location in the brain, but can spread in the course of the event; and generalized seizures, which can affect both hemispheres simultaneously. Partial seizures are manifested in multiple ways depending on the area that is affected (confusion, automatic body movements, hallucinations, etc), and if they spread in the brain can end up in a generalized tonic-clonic event (a convulsion). There are several types of generalized seizures: convulsive (tonic-clonic, tonic, clonic, myoclonic) and non-convulsive (absences, atonic). Typically all kinds of seizures last a few minutes, usually less than five minutes. Convulsive seizures, particularly tonic-clonic events, typically result in the loss of consciousness.

Status epilepticus (SE) has been defined as a seizure that lasts for 30 or more minutes, or a series of consecutive seizures that occur for 30 or more minutes during which the subject does not completely recover consciousness. Many clinicians and many recent major research articles, however, consider a patient to be in SE if seizures last more than 5 minutes. There are two main types of SE: generalized SE, which can be convulsive or non-convulsive, and focal SE. Generalized convulsive SE is the most severe type and is associated with high morbidity and mortality. SE can occur in patients with a prior diagnosis of epilepsy. However, the onset of SE is more frequent in subjects without previous epilepsy and is often related to a severe and acute brain disease (for example, encephalitis or stroke) or trauma. In addition to these, a variety of conditions including hypoglycemia, hyperthermia, drug overdose and alcohol or drug withdrawal can be a cause of SE. Thus, anticonvulsant activity of a compound or combination, for example in models for or patients with complex partial seizures, is not necessarily predictive for activity against SE. SE is not only a life threatening disease but also causes neuronal cell loss and epileptogenesis.

In spite of remarkable medical advances in the past 50 years, progress in epilepsy therapy has been quite inadequate for a large number of patients. The worldwide prevalence of epilepsy is estimated at between 0.3 and 0.6% (Sander et al., 1987; Schmidt et al., 1986; Loiseau; 1988). About 20-30% of patients suffer from intractable epilepsy or severe side effects despite early treatment and an optimum daily dosage of an adequate antiepileptic drug (Schmidt, 1992; Kramer, 1997; Brodie, 2001). In such cases, an alternative monotherapy may control the seizures; however, a complete suppression of convulsive attacks can be seldom achieved with an AED, even if it is administered at the maximally prescribed dose (Kramer, 1997). When monotherapy with antiepileptic drugs fails, combination therapy is tried in an attempt to improve effectiveness by improving efficacy, tolerability or both.

Lacosamide (LCM, R-2-acetamido-N-benzyl-3-methoxypropionamide) is a member of a series of functionalized amino acid with anticonvulsant activity. The anticonvulsant activity has been shown in large clinical studies and in animal models of epilepsy, including maximal electroshock seizure [MES], the 6 Hz refractory seizure model, and sound-induced seizure in Frings mice (Bialer et al., 2001, 2002; Hovinga 2003). Further, LCM is active against refractory self-sustaining status epilepticus. In addition to the activity of the drug in electrically induced seizures, it is effective against cobalt-homocysteine- and lithium-pilocarpine-induced status epilepticus (Bialer et al., 2001, 2002).

Initially there was a suggestion that LCM possessed affinity for the strychnine-insensitive glycine site of the NMDA receptor, however, further study suggest that this might not be a direct effect by which the drug exerts its anticonvulsant activity (Bialer et al., 2001, 2002). In receptor-binding studies (on more than 100 different sites), neither LCM nor its metabolites bind to a large variety of neurotransmitter receptors or ion channels (Errington et al. 2006). In cell/tissue culture, LCM had no effects on NMDA-evoked currents or at voltage gated sodium channels. In mouse cortical neurons, the drug increased GABA currents and inhibited glutamate transmission indirectly, most likely through non-specific mechanism (Bialer et al., 2002). Recent data indicate that LCM has a dual mode of action: it enhances slow inactivation of voltage-gated sodium channels and modulates collapsing response mediator protein CRMP-2.

The preclinical profile suggests that LCM will be useful in the treatment of partial onset and generalized tonic-clonic seizures. New antiepileptic drugs (AED) such as LCM are initially licensed as add-on treatment, often with no evidence to suggest which existing therapies they should be employed with. In addition, approximately 30% of patients with epilepsy are prescribed polytherapy regimens. There is, thus, a clear need to develop a rational basis for AED polytherapy, i.e. to develop anticonvulsant compositions with improved effectiveness by improving efficacy, tolerability, or both. Effective AED combinations were empirically evaluated in patients with intractable seizures; however, such evaluations were often accompanied with deleterious adverse-effect reactions (Warner et al., 1992; Luszczki et al., 2003). Thus, preclinical models are used as an alternative for the evaluation of pharmacodynamic drug interactions.

Pharmaceutical compositions comprising (a) a compound of a class of peptide compounds and (b) at least one further compound for the prevention, alleviation or/and treatment of epileptic seizures wherein the effect of this composition in the prevention, alleviation or/and treatment of epileptic seizures is synergistic as compared to the effect of the compounds (a) or (b) given alone have not been reported previously. Thus, the present invention concerns a pharmaceutical composition comprising (a) a compound of formula (I), (II) or/and (III) or a pharmaceutically acceptable salt thereof, and (b) at least one further compound for the prevention, alleviation or/and treatment of epileptic seizures optionally together with a pharmaceutically acceptable carrier, diluent or/and adjuvant. The effect of this composition in the prevention, alleviation or/and treatment of epileptic seizures may be synergistic as compared to the effect of the compounds (a) or (b) given alone.

The compound (b) is different from compound (a).

The term "synergistic effect on the prevention, alleviation or/and treatment of epileptic seizures" refers to an effect of the pharmaceutical composition according to the invention on the prevention, alleviation or/and treatment of epileptic seizures that is more than additive as compared to the effect of the compounds (a) or (b) given alone.

The synergistic effect of the present invention may be defined as a synergism of the combination of compounds (a) and (b) in a therapeutically desired effect (synergistic therapeutic effect) in the treatment of epileptic seizures.

The synergistic effect of the present invention may also be defined as a synergism of the combination of compounds (a) and (b) in reduction of adverse side effect, which may be smaller in the combination of compounds (a) and (b) as compared to the side effects of compounds (a) and (b) given alone.

According to Deckers et al. (2000) an isobolographic method used to evaluate interactions among AEDs is considered to be the optimal method for detecting synergy, additivity or antagonism among AEDs in animal models of epilepsy, such as the 6 Hz seizure model in mice. For isobolographic analysis, the experimental (EDmix) and theoretical additive (EDadd) ED50 values are determined from the dose-response curves of combined drugs. ED50 is defined as a dose of a drug protecting 50% of the animals against 6 Hz-induced seizures. ED50mix is an experimentally determined total dose of the mixture of two component drugs, which were administered in the fixed-ratio combination sufficient for a 50% protective effect. Conversely, ED50add represents a total additive dose of two drugs (calculated from the line of additivity), theoretically providing 50% protection against seizures.

The term "interaction index α" refers to the ratio of ED50mix/ED50add. This ratio seems to be a good describer of the strength of interaction between two AEDs in isobolographic analysis (Luszczki et al., 2003; Berenbaum, 1989; Tallarida et al., 1999; Tallarida, 2001, 2002). If ED50mix=ED50add, then α=1. Small derivations of α from 1 may not be considered as significant. If α is smaller than 0.7, this may indicate a synergistic effect. If the index is larger than 1.3, this may indicate an antagonistic effect, and if the index is in between this may indicate purely additive interaction (Luszczki et al., 2003; Kerry et al., 1975; Bourgeois, Wad, 1984, 1988; Bourgeois, 1988).

In a preferred embodiment, the synergistic effect of the pharmaceutical composition of the present invention is defined as a value of the interaction index α of the composition of up to about 0.7, preferably of up to about 0.6, more preferably of up to about 0.5, wherein α>0. Examples for the interaction index α are about 0.1, about 0.2, about 0.3, about 0.4, about 0.5, about 0.6, and about 0.7.

A protective index (PI) can be calculated by dividing a given TD50, determined in an animal model quantifying toxic effects of anticonvulsants, by the respective ED50 determined in an animal model for epileptic seizures. The PI is considered a satisfactory margin of safety between AED doses and doses of AEDs exerting sedative, ataxic, or other neurotoxic side effects (Löscher et al., 1991). $PI_{mix}$ is a protective index experimentally determined, and $PI_{add}$ is a protective index theoretically calculated from the lines of additivity in the epileptic seizure model and the model quantifying toxic effects.

The term "benefit index (BI)" refers to a quotient of $PI_{mix}$ and $PI_{add}$ of respective fixed-ratio combinations, obtained directly from the isobolographic analysis. BI unequivocally estimates advantages of the combination of two drugs applied in various fixed-ratio combinations. Moreover, BI may provide the rationale for combining the respective AEDs in clinical practice if its value is >1.3, whereas BI<0.7 may indicate unfavourable combinations of AEDs (Luszczki et al., 2003, Epilepsia 44: 489).

In another preferred embodiment, the synergistic effect of the pharmaceutical composition of the present invention is defined as a value of the benefit index BI of the composition of at least about 1.3, preferably of at least about 1.4, more preferably of at least about 1.5. Examples for the benefit index BI are about 1.3, about 1.4, about 1.5, about 1.6; about 1.7, about 1.8, about 1.9, and about 2.0.

The term "fixed-dose ratio of compound (b):compound (a) of 1:1, calculated on the ED50 values of the individual compounds (b) and (a)" refers to compositions comprising both compound (b) and compound (a) in a dose corresponding to 50% of the respective ED50 dose of the individual compounds (b) and (a) or a multiple of this fixed-dose ratio. Correspondingly, a "fixed-dose ratio of compound (b):compound (a) of 3:1, calculated on the ED50 values of the individual compounds (b) and (a)" refers to compositions comprising compound (b) in a dose corresponding to 75% of the respective ED50 dose and compound (a) in a dose corresponding to 25% of the respective ED50 dose of compound (a) or a multiple of this fixed-dose ratio.

In general, the "fixed-dose ratio of compound (b):compound (a) of X:Y, calculated on the ED50 values of the individual compounds (b) and (a)" refers to compositions comprising both compound (b) and compound (a), wherein the dose of compound (b) corresponds to $X \cdot ED_{50}/(X+Y)$ of compound (b), and the dose of compound (a) corresponds to $Y \cdot ED_{50}/(X+Y)$ of compound (a), or a multiple of this fixed dose ratio.

Thus, a composition comprising both compound (b) and compound (a) in a fixed dose ratio of at least X:Y comprises at least X/(at least X+Y) parts of compound (b), wherein 1 part is an amount corresponding to the ED50 of compound (b), and Y/(at least X+Y) parts of compound (a), wherein 1 part is an amount corresponding to the ED50 of compound (a), or a multiple of this fixed dose ratio.

The term "multiple" refers to a composition comprising a larger or a smaller amount of compounds (a) and (b) with reference to the amount as defined by the ED50 values, while maintaining the fixed dose ratio. A composition comprising a multiple of the fixed dose ratio as indicated above may thus comprise at least 0.1 times the fixed dose ratio, at least 0.2 times, at least 0.5 times, at least 2 times, at least 5 times, or at least 10 times the fixed dose ratio, or/and at the maximum 100 times the fixed dose ratio, at the maximum 50 times, or at the maximum 20 times the fixed dose ratio.

In yet another preferred embodiment, compound (b) and compound (a) are present in the pharmaceutical composition of the present invention in a fixed-dose ratio of compound (b):compound (a) of about 1:6 to about 6:1, preferably of about 1:3 to about 6:1, more preferably of about 1:1 to about 6:1, even more preferably of about 3:1 to about 6:1, wherein the fixed-dose ratio is calculated on the $ED_{50}$ values of the individual compounds (b) and (a). Examples for fixed-dose ratios of compound (b):compound (a) according to the present invention are fixed-dose ratios of about 1:6, about 1:3, about 1:1, about 3:1, and about 6:1. Further examples for fixed-dose ratios according to the present invention are fixed-dose ratios of about 1:5, about 1:4, about 1:2, about 2:1, about 4:1, and about 5:1.

In a preferred embodiment, compound (b) and compound (a) are present in the pharmaceutical composition of the present invention in a fixed-dose ratio of compound (b):compound (a) of at least about 1:6, at least about 1:3, at least about 1:1, more preferably at least about 3:1, wherein the fixed-dose ratio is calculated on the $ED_{50}$ values of the individual compounds (b) and (a). Examples for fixed-dose ratios of compound (b):compound (a) according to this more preferred embodiment of the present invention are fixed-dose ratios of about 1:1, about 2:1, about 3:1, about 4:1, about 5:1, and about 6:1.

In yet another preferred embodiment, compound (b) and compound (a) are present in the pharmaceutical composition of the present invention in a fixed-dose ratio of compound (b):compound (a) of at the maximum about 6:1, wherein the fixed-dose ratio is calculated on the $ED_{50}$ values of the individual compounds (b) and (a).

In another preferred embodiment, compound (b) of the pharmaceutical composition of the present invention is selected from the group consisting of racetams, gamma amino butyric acid analogs, dibenzazepines, phenyltriazine derivatives, monosaccharide sulfamates, hydantoin derivatives, and barbiturates. The racetam may be selected from the group consisting of piracetam, aniracetam, oxiracetam, pramiracetam, phenylpiracetam, etiracetam, levetiracetam, nefiracetam, rolziracetam, nebracetam, fasoracetam, coluracetam, brivacetam, and seletracetam. The gamma amino butyric acid analog may be selected from the group consisting of gapapentin and pregabalin. The dibenzazepine may be carbamazepine. The phenyltriazine derivative may lamotrigine. The monosaccharide sulfamate may be topiramate. The hydantoin derivative may be selected from the group consisting of ethotoin, phenyloin, mephenyloin, and fosphenyloin. The barbiturate may be selected from the group consisting of phenobarbital, methylphenobarbital, metharbital, pentobarbital, and barbexaclone.

In yet another preferred embodiment, compound (b) of the pharmaceutical composition of the present invention is selected from the group comprising levetiracetam, lamotrigine, carbamazepine, topiramate, gabapentin, brivaracetam, seletracetam, zonisamide, felbamate, tiagabine, vigabatrine, diazepam, midazolam, phenobarbital, pentobarbital, and ethosuximide.

In yet another preferred embodiment, compound (b) of the pharmaceutical composition of the present invention is selected from the group consisting of levetiracetam, lamotrigine, carbamazepine, topiramate, gabapentin, brivaracetam, seletracetam, zonisamide, felbamate, tiagabine, vigabatrine, diazepam, midazolam, pentobarbital, and ethosuximide.

More preferably, compound (b) of the pharmaceutical composition of the present invention is selected from the group comprising levetiracetam, lamotrigine, carbamazepine, topiramate, brivaracetam, seletracetam, and ethosuximide. Even more preferably, compound (b) of the pharmaceutical composition of the present invention is selected from the group comprising levetiracetam, carbamazepine, brivaracetam, seletracetam, and ethosuximide. Most preferably, compound (b) of the pharmaceutical composition of the present invention is selected from the group comprising levetiracetam, brivaracetam, seletracetam.

The skilled person may determine the ED50 values by methods known in the art. It is preferred that the ED50 values are determined by preclinical or/and clinical trials. Published ED50 values may also be used. ED50 values are published for instance for lacosamide, lamotrigine, carbamazepine, topiramate, levetiracetam, gabapentin. FIGS. 12 and 13 disclose specific ED50 values obtained in various models of the rat and the mouse. A person skilled in the art knows that in a particular model, among different species, ED50 values show a variation by a factor of up to 5 or even larger.

In particular, the ED50 of lacosamide is in a range of at least about 0.5 mg/kg up to about 30 mg/kg body weight p.o. or i.p. More particularly, the ED50 of lacosamide is about 10 mg/kg body weight i.p.

In particular, the ED50 of lamotrigine is in a range of at least about 1 mg/kg up to about 10 mg/kg body weight p.o. or i.p. The ED50 of lamotrigine may also be about 85 mg/kg body weight i.p.

In particular, the ED50 of carbamazepine is in a range of at least about 3 mg/kg up to about 30 mg/kg body weight p.o. or i.p. The ED50 of carbamazepine may also be about 50 mg/kg body weight i.p.

In particular, the ED50 of levetiracetam in a range of at least about 10 mg/kg up to about 100 mg/kg body weight p.o. or i.p. More particularly, the ED50 of levetiracetam is about 20 mg/kg body weight i.p.

In particular, the ED50 of topiramate is in a range of at least about 5 mg/kg up to about 500 mg/kg body weight p.o. or i.p. More particularly, the ED50 of topiramate is about 300 mg/kg body weight i.p.

In particular, the ED50 of gabapentin is in a range of at least about 5 mg/kg up to about 100 mg/kg body weight p.o. or i.p. The ED50 of gabapentin may also be about 220 mg/kg body weight i.p.

Levetiracetam is the ethyl derivative of piracetam and belongs to the group of racetams. Racetams may have a synergistic effect in the prevention, alleviation or/and treatment of epileptic seizures, as compared to the effect of lacosamide and a racetam alone, wherein epileptic seizures are as defined herein.

Another particularly preferred pharmaceutical composition of the present invention comprises a racetam and lacosamide or/and a pharmaceutically acceptable salt thereof, optionally together with a pharmaceutically acceptable carrier, diluent or/and adjuvant. The racetam may be selected from the group consisting of piracetam, aniracetam, oxiracetam, pramiracetam, phenylpiracetam, etiracetam, levetiracetam, nefiracetam, rolziracetam, nebracetam, fasoracetam, coluracetam, brivacetam, and seletracetam.

Gabapentin is a gamma amino butyric acid analog. Gamma amino butyric acid analogs may have a synergistic effect in the prevention, alleviation or/and treatment of epileptic seizures, as compared to the effect of lacosamide and a gamma amino butyric acid analog alone, wherein epileptic seizures are as defined herein.

Another particularly preferred pharmaceutical composition of the present invention comprises a gamma amino butyric acid analog and lacosamide or/and a pharmaceutically acceptable salt thereof, optionally together with a pharmaceutically acceptable carrier, diluent or/and adjuvant. The gamma amino butyric acid analog may be selected from the group consisting of gapapentin and pregabalin.

Carbamazepine is a dibenzazepine. Dibenzazepines may have a synergistic effect in the prevention, alleviation or/and treatment of epileptic seizures, as compared to the effect of lacosamide and a dibenzazepine alone, wherein epileptic seizures are as defined herein.

Another particularly preferred pharmaceutical composition of the present invention comprises a dibenzazepine and lacosamide or/and a pharmaceutically acceptable salt thereof, optionally together with a pharmaceutically acceptable carrier, diluent or/and adjuvant. The dibenzazepine may be carbamazepine.

Lamotrigine is a phenyltriazine derivative. Phenyltriazine derivatives may have a synergistic effect in the prevention, alleviation or/and treatment of epileptic seizures, as compared to the effect of lacosamide and a phenyltriazine derivative alone, wherein epileptic seizures are as defined herein.

Another particularly preferred pharmaceutical composition of the present invention comprises a phenyltriazine derivative and lacosamide or/and a pharmaceutically acceptable salt thereof, optionally together with a pharmaceutically acceptable carrier, diluent or/and adjuvant. The phenyltriazine derivative may lamotrigine.

Topiramate is a monosaccharide sulfamate. Monosaccharide sulfamates may have a synergistic effect in the prevention, alleviation or/and treatment of epileptic seizures, as compared to the effect of lacosamide and a monosaccharide sulfamate, wherein epileptic seizures are as defined herein.

Another particularly preferred pharmaceutical composition of the present invention comprises a monosaccharide sulfamate and lacosamide or/and a pharmaceutically acceptable salt thereof, optionally together with a pharmaceutically acceptable carrier, diluent or/and adjuvant. The monosaccharide sulfamate may be topiramate.

Phenyloin is a hydantoin derivative. Hydantoin derivatives may have a synergistic effect in the prevention, alleviation or/and treatment of epileptic seizures, as compared to the effect of lacosamide and the hydantoin derivative alone, wherein epileptic seizures are as defined herein.

Another particularly preferred pharmaceutical composition of the present invention comprises a hydantoin derivative and lacosamide or/and a pharmaceutically acceptable salt thereof, optionally together with a pharmaceutically acceptable carrier, diluent or/and adjuvant. The hydantoin derivative may be selected from the group consisting of ethotoin, phenyloin, mephenyloin, and fosphenyloin.

Phenobarbital is a barbiturate. Barbiturates may have a synergistic effect in the prevention, alleviation or/and treatment of epileptic seizures, as compared to the effect of lacosamide and a barbiturate alone, wherein epileptic seizures are as defined herein.

Another particularly preferred pharmaceutical composition of the present invention comprises a barbiturate and lacosamide or/and a pharmaceutically acceptable salt thereof, optionally together with a pharmaceutically acceptable carrier, diluent or/and adjuvant. The barbiturate may be selected from the group consisting of phenobarbital, methylphenobarbital, metharbital, pentobarbital, and barbexaclone.

A particularly preferred pharmaceutical composition of the present invention comprises levetiracetam and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and levetiracetam alone, wherein epileptic seizures are as defined herein.

In this particularly preferred composition, levetiracetam and lacosamide may be present in a fixed-dose ratio of levetiracetam:lacosamide of at least about 1:3, at least about 1:1, or at least about 3:1, wherein the fixed-dose ratio is calculated on the individual ED50 values of levetiracetam and lacosamide. In this particularly preferred composition, the fixed-dose ratio of levetiracetam:lacosamide may be at the maximum about 6:1. The fixed dose ratio may be calculated on the basis of a levetiracetam ED50 value or/and a lacosamide ED50 value disclosed herein, or on the basis of ED50 values known in the art.

This particularly preferred composition may comprise levetiracetam in a dose of at least 1000 mg/day up to 3000 mg/day and lacosamide in a dose of at least of 100 mg/day, preferably at least of 200 mg/day, more preferably at least of 300 mg/day, most preferably at least of 400 mg/day, and in a dose of at a maximum of 6 g/day, more preferably at a maximum of 1 g/day and most preferably at a maximum of 600 mg/day.

Another particularly preferred pharmaceutical composition of the present invention comprises brivaracetam and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and brivaracetam alone, wherein epileptic seizures are as defined herein.

In this particularly preferred composition, brivaracetam and lacosamide may be present in a fixed-dose ratio of brivaracetam:lacosamide of at least about 1:3, at least about 1:1, or at least about 3:1, wherein the fixed-dose ratio is calculated on the individual ED50 values of brivaracetam and lacosamide. In this particularly preferred composition, the fixed-dose ratio of brivaracetam:lacosamide may be at the maximum about 6:1. The fixed dose ratio may be calculated on the basis of a brivaracetam ED50 known in the art or/and on the basis of a lacosamide ED50 value disclosed herein or known in the art.

Yet another particularly preferred pharmaceutical composition of the present invention comprises seletracetam and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and seletracetam alone, wherein epileptic seizures are as defined herein.

In this particularly preferred composition, seletracetam and lacosamide may be present in a fixed-dose ratio of seletracetam:lacosamide of at least about 1:3, at least about 1:1, or at least about 3:1, wherein the fixed-dose ratio is calculated on the individual ED50 values of seletracetam and lacosamide. In this particularly preferred composition, the fixed-dose ratio of seletracetam:lacosamide may be at the maximum about 6:1. The fixed dose ratio may be calculated on the basis of a seletracetam ED50 value known in the art or/and on the basis of a lacosamide ED50 value disclosed herein or known in the art.

Another particularly preferred pharmaceutical composition of the present invention comprises lamotrigine and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and lamotrigine alone, wherein epileptic seizures are as defined herein.

In this particularly preferred composition, lamotrigine and lacosamide may be present in a fixed-dose ratio of lamotrigine:lacosamide of at least about 1:3, at least about 1:1, or at least about 3:1, wherein the fixed-dose ratio is calculated on the individual ED50 values of lamotrigine and lacosamide. In this particularly preferred composition, the fixed-dose ratio of lamotrigine:lacosamide may be at the maximum about 6:1. The fixed dose ratio may be calculated on the basis of a lamotrigine ED50 value or/and a lacosamide ED50 value disclosed herein or on the basis of ED50 values known in the art.

This particularly preferred composition may comprise lamotrigine in a dose of at least 100 mg/day up to 400 mg/day and lacosamide in a dose of at least of 100 mg/day, preferably at least of 200 mg/day, more preferably at least of 300 mg/day, most preferably at least of 400 mg/day, and in a dose of at a maximum of 6 g/day, more preferably at a maximum of 1 g/day and most preferably at a maximum of 600 mg/day.

Yet another particularly preferred pharmaceutical composition of the present invention comprises carbamazepine and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and carbamazepine alone, wherein epileptic seizures are as defined herein.

In this particularly preferred composition, carbamazepine and lacosamide may be present in a fixed-dose ratio of carbamazepine:lacosamide of at least about 1:3, at least about 1:1, or at least about 3:1, wherein the fixed-dose ratio is calculated on the individual ED50 values of carbamazepine and lacosamide. In this particularly preferred composition, the fixed-dose ratio of carbamazepine:lacosamide may be at the maximum about 6:1. The fixed dose ratio may be calculated on the basis of a carbamazepine ED50 value or/and a lacosamide ED50 value disclosed herein, or on the basis of ED50 values known in the art.

This particularly preferred composition may comprise carbamazepine in a dose of at least 400 mg/day up to 1600 mg/day and lacosamide in a dose of at least of 100 mg/day, preferably at least of 200 mg/day, more preferably at least of 300 mg/day, most preferably at least of 400 mg/day, and in a dose of at a maximum of 6 g/day, more preferably at a maximum of 1 g/day and most preferably at a maximum of 600 mg/day.

Another particularly preferred pharmaceutical composition of the present invention comprises topiramate and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and topiramate alone, wherein epileptic seizures are as defined herein.

In this particularly preferred composition, topiramate and lacosamide may be present in a fixed-dose ratio of topiramate:lacosamide of at least about 1:3, at least about 1:1, or at least about 3:1, wherein the fixed-dose ratio is calculated on the individual ED50 values of topiramate and lacosamide. In this particularly preferred composition, the fixed-dose ratio of topiramate:lacosamide may be at the maximum about 6:1. The fixed dose ratio may be calculated on the basis of a topiramate ED50 value or/and a lacosamide ED50 value disclosed herein, or on the basis of ED50 values known in the art.

This particularly preferred composition may comprise topiramate in a dose of at least 200 mg/day up to 400 mg/day and lacosamide in a dose of at least of 100 mg/day, preferably at least of 200 mg/day, more preferably at least of 300 mg/day, most preferably at least of 400 mg/day, and in a dose of at a maximum of 6 g/day, more preferably at a maximum of 1 g/day and most preferably at a maximum of 600 mg/day.

Another particularly preferred pharmaceutical composition of the present invention comprises gabapentin and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and gabapentin alone, wherein epileptic seizures are as defined herein.

In this particularly preferred composition, gabapentin and lacosamide may be present in a fixed-dose ratio of gabapentin:lacosamide of at least about 1:3, at least about 1:1, or at least about 3:1, wherein the fixed-dose ratio is calculated on the individual ED50 values of gabapentin and lacosamide. In this particularly preferred composition, the fixed-dose ratio of gabapentin:lacosamide may be at the maximum about 6:1. The fixed dose ratio may be calculated on the basis of a gabapentin ED50 value or/and a lacosamide ED50 value disclosed herein, or on the basis of ED50 values known in the art.

This particularly preferred composition may comprise gabapentin in a dose of at least 900 mg/day up to 3600 mg/day and lacosamide in a dose of at least of 100 mg/day, preferably at least of 200 mg/day, more preferably at least of 300 mg/day, most preferably at least of 400 mg/day, and in a dose of at a maximum of 6 g/day, more preferably at a maximum of 1 g/day and most preferably at a maximum of 600 mg/day.

Another particularly preferred pharmaceutical composition of the present invention comprises ethosuximide and lacosamide or/and a pharmaceutically acceptable salt thereof, optionally together with a pharmaceutically acceptable carrier, diluent or/and adjuvant.

This particularly preferred composition may have a synergistic effect in the prevention, alleviation or/and treatment of epileptic seizures, as compared to the effect of lacosamide and ethosuximide alone, wherein epileptic seizures are as defined herein.

In this particularly preferred composition, ethosuximide and lacosamide may be present in a fixed-dose ratio of ethosuximide:lacosamide of at least about 1:3, at least about 1:1, or at least about 3:1, wherein the fixed-dose ratio is calculated on the individual ED50 values of ethosuximide and lacosamide. In this particularly preferred composition, the fixed-dose ratio of ethosuximide:lacosamide may be at the maximum about 6:1. The fixed dose ratio may be calculated on the basis of a ethosuximide ED50 value or/and a lacosamide ED50 value disclosed herein, or on the basis of ED50 values known in the art.

This particularly preferred composition of ethosuximide and lacosamide may comprise ethosuximide in a dose commonly known by a physician, such as at least 15 mg/kg body weight up to 40 mg/kg body weight or/and about 1 g/day, and lacosamide in a dose of at least of 100 mg/day, preferably at least of 200 mg/day, more preferably at least of 300 mg/day, most preferably at least of 400 mg/day, and in a dose of at a maximum of 6 g/day, more preferably at a maximum of 1 g/day and most preferably at a maximum of 600 mg/day.

In the particularly preferred compositions described herein, the synergistic effect may also be defined in terms of the interaction index α, as described herein, or in terms of the benefit index, as described herein.

The particularly preferred pharmaceutical compositions described herein may preferably be prepared for i.v. or oral administration.

In another preferred embodiment, compound (b) of the pharmaceutical composition of the present invention is not a compound selected from the group consisting of valproate, phenyloin, phenbarbitol (phenobarbital), and mephenyloin.

In another preferred embodiment, compound (b) of the pharmaceutical composition of the present invention is not a compound selected from the group consisting of phenyloin, phenbarbitol (phenobarbital), and mephenyloin.

In another preferred embodiment, compound (b) of the pharmaceutical composition of the present invention is not valproate or phenyloin.

Combinations of valproate or phenyloin with lacosamide seem to exhibit only a small non-significant synergistic therapeutic effect in treatment of epileptic seizures. It is thus more preferred that in those embodiments of the present invention relating to a synergistic therapeutic effect, compound (b) of the pharmaceutical composition is not valproate or phenyloin.

In yet another embodiment of the present invention, the synergistic effect of the pharmaceutical composition of the present invention is defined as a reduced adverse effect of the combination of compound (a) and compound (b) as compared with the compounds (a) and (b) given alone.

A synergistic side effect reduction may not only be found in those combinations exhibiting a synergistic therapeutic effect, but may also be found in those combinations of compounds (a) and (b) exhibiting an additive therapeutic effect or a non-significant synergistic therapeutic effect in the treatment of epileptic seizures, such as, for instance, valproate or phenyloin being compound (b) combined with lacosamide.

Thus, subject of a preferred embodiment of the present invention are combinations of a compound (a) as defined herein with valproate or phenyloin, wherein the synergistic effect may be a reduced adverse effect of the combination of compound (a) and valproate or phenyloin, as compared with the compounds (a) and valproate or phenyloin given alone. More preferred are combinations of valproate and lacosamide or phenyloin and lacosamide.

In a preferred embodiment, the epileptic seizures are selected from partial seizures with and without secondary generalisation, primarily generalised seizures, and status epilepticus.

Yet another aspect of the present invention is the use of the pharmaceutical composition of the invention for the preparation of a medicament for the prevention, alleviation or/and treatment of epileptic seizures, wherein epileptic seizures are as defined herein.

Yet another aspect of the present invention is a method for the prevention, alleviation or/and treatment of epileptic seizures, wherein epileptic seizures are as defined herein, comprising administering an effective amount of the pharmaceutical composition of the invention to a subject in need thereof.

The compounds of the present invention of Formulae (I), (II) or/and (III), in particular lacosamide, are well tolerated, which is an advantage over other commonly used therapeutics for treatment of epileptic seizures.

The compound of Formulae (I), (II) or/and (III) as described herein and the compound (b) may be formulated in one pharmaceutical preparation (single dosage form) for administration at the same time or may be formulated in two or more distinct preparations (separate dosage forms), which separate dose forms may be administered simultaneously or/and subsequently. The distinct preparations in the separate dosage forms may be administered by the same route or by different routes.

The pharmaceutical composition of the present invention may thus comprise a single dosage form comprising at least one compound of Formulae (I), (II), or/and (III) and at least one compound (b).

The pharmaceutical composition of the present invention may also comprise a separate dosage form comprising
(i) a first composition comprising at least one compound of Formulae (I), (II), or/and (III), and
(ii) a second composition comprising at least one compound (b).

In yet another preferred embodiment of the present invention, the second composition (ii) may be a commercially available composition.

Separate dosage forms can optionally be co-packaged, for example in a single container or in a plurality of containers within a single outer package, or co-presented in separate packaging ("common presentation"). As an example of co-packaging or common presentation, a kit is contemplated comprising, in separate containers, the compound of Formulae (I), (II) or/and (III) and compound (b). In another example, the compound of Formulae (I), (II), or/and (III) and the compound (b) are separately packaged and available for sale independently of one another, but are co-marketed or co-promoted for use according to the invention. The separate dose forms may also be presented to a subject separately and independently, for use according to the invention.

The pharmaceutical composition of the present invention is preferably prepared for administration in mammals, preferably in humans.

The pharmaceutical composition of the present invention comprising (a) at least one compound of Formulae (I), (II) or/and (III) and at least one compound (b) may be prepared for the prevention, alleviation or/and treatment of epileptic seizures, as defined herein.

The administration interval of the compound of Formulae (I), (II), or/and (III) and the compound (b) may depend on the dosage forms. The compound of Formulae (I), (II), or/and (III) may be administered first, or the compound (b) may be administered first.

The compound (a) is a compound of Formulae (I), (II) or/and (III).

The compound (a) according to the invention has the general Formula (I)

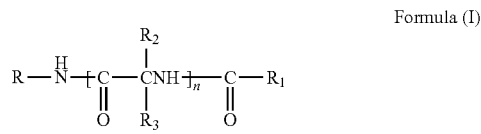

Formula (I)

wherein

R is hydrogen, alkyl, alkenyl, alkynyl, aryl, aryl alkyl, heterocyclic, heterocyclic alkyl, alkyl heterocyclic, cycloalkyl or cycloalkyl alkyl, and R is unsubstituted or is substituted with at least one electron withdrawing group, or/and at least one electron donating group;

$R_1$ is hydrogen or alkyl, alkenyl, alkynyl, aryl alkyl, aryl, heterocyclic alkyl, alkyl heterocyclic, heterocyclic, cycloalkyl, cycloalkyl alkyl, each unsubstituted or substituted with at least one electron donating group or/and at least one electron withdrawing group;

and $R_2$ and $R_3$ are independently hydrogen, alkyl, alkenyl, alkynyl, alkoxy, alkoxyalkyl, aryl alkyl, aryl, halo, heterocyclic, heterocyclic alkyl, alkyl heterocyclic, cycloalkyl, cycloalkyl alkyl, or Z—Y wherein $R_2$ and $R_3$ may be unsubstituted or substituted with at least one electron withdrawing group or/and at least one electron donating group;

Z is O, S, $S(O)_a$, $NR_4$, $NR'_6$, $PR_4$ or a chemical bond;

Y is hydrogen, alkyl, aryl, aryl alkyl, alkenyl, alkynyl, halo, heterocyclic, heterocyclic alkyl, alkyl heterocyclic and Y may be unsubstituted or substituted with at least one electron donating group or/and at least one electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$ or $N^+R_5R_6R_7$,

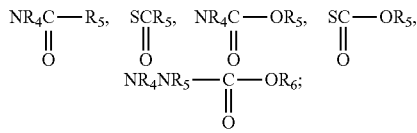

$R'_6$ is hydrogen, alkyl, alkenyl, or alkenyl which may be unsubstituted or substituted with at least one electron withdrawing group or/and at least one electron donating group;

$R_4$, $R_5$ and $R_6$ are independently hydrogen, alkyl, aryl, aryl alkyl, alkenyl, or alkynyl, wherein $R_4$, $R_5$ and $R_6$ may independently be unsubstituted or substituted with at least one electron withdrawing group or/and at least one electron donating group;

$R_7$ is $R_6$ or $COOR_8$ or $COR_8$, which $R_7$ may be unsubstituted or substituted with at least one electron withdrawing group or/and at least one electron donating group;

$R_8$ is hydrogen or alkyl, or aryl alkyl, and the aryl or alkyl group may be unsubstituted or substituted with at least one electron withdrawing group or/and at least one electron donating group; and n is 1-4; and a is 1-3.

In a preferred embodiment, the compound of Formula (I) has the general Formula (II),

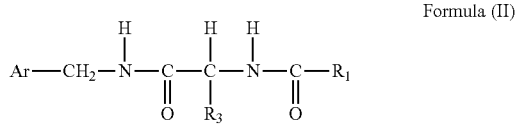

Formula (II)

wherein

Ar is aryl which is unsubstituted or substituted with at least one electron donating group or/and at least one electron withdrawing group, preferably halo, more preferably fluoro;

$R_1$ is alkyl, preferably alkyl containing 1-3 carbon atoms, more preferably methyl; and $R_3$ is as defined herein.

In a more preferred embodiment, the compound of Formulae (I) or/and (II) has the general Formula (III),

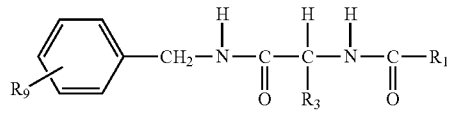

Formula (III)

wherein $R_9$ is one or more substituents independently selected from the group consisting of hydrogen, halo, alkyl, alkenyl, alkynyl, nitro, carboxy, formyl, carboxyamido, aryl, quaternary ammonium, haloalkyl, aryl alkanoyl, hydroxy, alkoxy, carbalkoxy, amino, alkylamino, dialkylamino, aryloxy, mercapto, alkylthio, alkylmercapto, and disulfide;

$R_3$ is selected from the group consisting of hydrogen, alkyl, arylalkyl, alkoxy, alkoxyalkyl, aryl, heterocyclic, heterocyclic alkyl, N-alkoxy-N-alkylamino, N-alkoxyamino, and N-carbalkoxy; and $R_1$ is alkyl, preferably alkyl containing 1 to 3 carbon atoms, more preferably methyl.

The compounds (a) utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

As used herein, the term configuration particularly refers to the configuration around the carbon atom to which $R_2$ and $R_3$ or H and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ or H and $R_3$ are attached. However, it also includes all possible enantiomers and diastereomers at other chiral centers, if any, present in the compound.

The compounds (a) of the present invention are directed to all the optical isomers, i.e., the compounds of the present invention are either the L-stereoisomer or the D-stereoisomer (at the carbon atom to which $R_2$ and $R_3$ or H and $R_3$ are attached). These stereoisomers may be found in mixtures of the L and D stereoisomer, e.g., racemic mixtures. The D stereoisomer is preferred.

It is preferred that the compounds of Formula (I) are in the R configuration. It is also preferred that the compounds of Formula (II) are in the R configuration. It is also preferred that the compounds of Formula (III) are in the R configuration.

It is preferred that the compounds of Formulae (I), (II) or/and (III) in the R configuration are substantially enantiopure. As used herein, the term "substantially enantiopure" refers to a content of the R enantiomer of at least 99.5%. This corresponds to an enantiomeric excess (ee) of 99%. The respective quantities of R and S enantiomer may be determined by chiral column chromatography, e.g. by HPLC with "ChiralPak" as chiral, stationary phase.

The term "alkyl" (alone or in combination with another term(s)) means a straight- or branched-chain saturated hydrocarbyl substituent preferably containing from 1 to about 20 carbon atoms ($C_1$-$C_{20}$-alkyl), more preferably from 1 to about 8 carbon atoms ($C_1$-$C_8$-alkyl), even more preferably from 1 to about 6 carbon atoms ($C_1$-$C_6$-alkyl), and most preferably from 1 to 3 carbon atoms ($C_1$-$C_3$-alkyl). The alkyl groups include methyl, ethyl, propyl, isopropyl, butyl, isobutyl, tertiary butyl, amyl, hexyl, and the like. Further, alkyl groups also include halogenated alkyl groups up to perhalogenation, e.g. trifluoromethyl, if not indicated otherwise.

The term "alkoxy" (alone or in combination with another term(s)) refers to —O-alkyl and means a straight- or branched-chain alkoxy substituent preferably containing from 1 to about 20 carbon atoms ($C_1$-$C_{20}$-alkoxy), more preferably from 1 to about 8 carbon atoms ($C_1$-$C_8$-alkoxy), even more preferably from 1 to about 6 carbon atoms ($C_1$-$C_6$-alkoxy), and most preferably from 1 to 3 carbon atoms ($C_1$-$C_3$-alkoxy). The alkoxy groups include methoxy, ethoxy, propoxy, butoxy, isobutoxy, tert-butoxy, pentoxy, hexoxy and the like. Further, alkoxy groups include halogenated alkoxy groups up to perhalogenation, if not indicated otherwise.

The term "alkoxyalkyl" refers to an alkyl group substituted with at least one alkoxy group. The alkoxyalkyl groups include methoxymethyl (—$CH_2$—$OCH_3$) groups, methoxyethyl (—$CH_2$—$CH_2$—$OCH_3$) groups, ethoxymethyl (—$CH_2$—O—$CH_2CH_3$) groups and the like.

The term "N-alkoxyamino" refers to amino groups substituted with one or two alkoxy groups, e.g. —NH—N($OCH_3$)$_2$.

The term "N-alkoxy-N-alkylamino" refers to amino groups substituted with an alkoxy group and an alkyl group, e.g. —N($CH_3$)($OCH_3$), —N($CH_3$)($OCH_2$—$CH_3$) and the like.

The term "N-carbalkoxy" refers to amino groups substituted with a carbalkoxy group, e.g. —NH(C(O)—O—$CH_3$), —NH(C(O)O—$CH_2$—$CH_3$).

The term "aryl", when used alone or in combination with other term(s), refers to an aromatic group which contains from 6 up to 18 ring carbon atoms ($C_6$-$C_{18}$-aryl), preferably from 6 up to 10 ring carbon atoms ($C_6$-$C_{10}$-aryl), and includes polynuclear aromatics. The aryl groups may be monocyclic, bicyclic, tricyclic or polycyclic and may be fused rings. A polynuclear aromatic compound as used herein, is meant to encompass bicyclic and tricyclic fused aromatic ring systems containing from 10-18 ring carbon atoms. Aryl groups include phenyl and polynuclear aromatics e.g., naphthyl, anthracenyl, phenanthrenyl, azulenyl and the like. The aryl group also includes groups such as ferrocenyl. Aryl groups may be unsubstituted or mono or polysubstituted with electron withdrawing or/and electron donating groups. A preferred aryl group is phenyl, which may unsubstituted or mono or polysubstituted with electron withdrawing or/and electron donating groups.

The term "aryl alkyl" as used herein alone or in combination with other term (s) means an alkyl group as defined herein carrying an aryl substitutent as defined herein. Preferred aryl alkyl groups are aryl-$C_1$-$C_6$-alkyl, aryl-$C_1$-$C_3$-alkyl, $C_6$-$C_{10}$-aryl-alkyl, $C_6$-$C_{10}$-aryl-$C_1$-$C_6$-alkyl, $C_6$-$C_{10}$-aryl-$C_1$-$C_3$-alkyl. More preferred aryl alkyl groups are phenyl-$C_1$-$C_6$-alkyl and phenyl-$C_1$-$C_3$-alkyl. Even more preferred aryl alkyl groups include, for example, benzyl, phenylethyl, phenylpropyl, phenylisopropyl, phenylbutyl, diphenylmethyl, 1,1-diphenylethyl, 1,2-diphenylethyl, and the like. Most preferred is benzyl.

The term "alkenyl" (alone or in combination with another term(s)) means a straight- or branched-chain alkenyl substituent containing at least one double bond and preferably containing from 2 to about 20 carbon atoms ($C_2$-$C_{20}$-alkenyl), more preferably from 2 to about 8 carbon atoms ($C_2$-$C_8$-alkenyl), and even more preferably from 2 to about 6 carbon atoms ($C_2$-$C_6$-alkenyl), most preferably 2 or 3 carbon atoms ($C_2$-$C_3$-alkenyl). The alkenyl group may be in the Z or E form. Alkenyl groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term "alkynyl" (alone or in combination with another term(s)) means a straight- or branched-chain alkynyl substituent containing at least one triple bond and preferably containing from 2 to about 20 carbon atoms ($C_2$-$C_{20}$-alkynyl), more preferably from 2 to about 8 carbon atoms ($C_2$-$C_8$-alkynyl), and even more preferably from 2 to about 6 carbon atoms ($C_2$-$C_6$-alkynyl), most preferably 2 or 3 carbon atoms ($C_2$-$C_3$-alkynyl). The alkynyl group includes ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "cycloalkyl" when used alone or in combination with another term (s) means a cycloalkyl group containing from 3 to 18 ring carbon atoms ($C_3$-$C_{18}$-cycloalkyl), preferably from 6 up to 10 ring carbon atoms ($C_3$-$C_{10}$-cycloalkyl). The cycloalkyl groups may be monocyclic, bicyclic, tricyclic, or polycyclic, and the rings may be fused. The cycloalkyl may be completely saturated or partially saturated. Examples of cycloalkyl groups include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. The cycloalkyl group includes the cis or trans forms. Cycloalkyl groups may be unsubstituted or mono or polysubstituted with electron withdrawing or/and electron donating groups. In a bridged bicyclic cycloalkyl group, the substituents may either be in endo or exo positions.

The term "cycloalkyl alkyl" as used herein alone or in combination with other term(s) means an alkyl group as defined herein carrying a cycloalkyl substitutent as defined herein. Preferred cycloalkyl alkyl groups are cycloalkyl-$C_1$-$C_6$-alkyl, cycloalkyl-$C_1$-$C_3$-alkyl, $C_6$-$C_{10}$-cycloalkyl-alkyl, $C_6$-$C_{10}$-cycloalkyl-$C_1$-$C_6$-alkyl, $C_6$-$C_{10}$-cycloalkyl-$C_1$-$C_3$-alkyl. A more preferred cycloalkyl alkyl group is selected from cyclohexyl-$C_1$-$C_6$-alkyl and cyclohexyl-$C_1$-$C_3$-alkyl.

The term "halo" or "halogen" includes fluoro, chloro, bromo, and iodo.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Examples of haloalkyls include chloromethyl, 1-bromoethyl, fluoromethyl, difluoromethyl, trifluoromethyl, 1,1,1-trifluoroethyl, and the like. Illustrating further, "haloalkoxy" means an alkoxy substituent wherein at least one hydrogen radical is replaced by a halogen radical. Examples of haloalkoxy substituents include chloromethoxy, 1-bromoethoxy, fluoromethoxy, difluoromethoxy, trifluoromethoxy (also known as "perfluoromethyloxy"), 1,1,1,-trifluoroethoxy, and the like. It should be recognized that if a substituent is substituted by more than one halogen radical, those halogen radicals may be identical or different (unless otherwise stated).

The terms "electron-withdrawing" and "electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo; nitro, carboxy, alkenyl, alkynyl, formyl, carboxyamido, aryl, quaternary ammonium, haloalkyl such as trifluoromethyl, aryl alkanoyl, carbalkoxy and the like. Electron donating groups include such groups as hydroxy, alkoxy, including methoxy, ethoxy and the like; alkyl, such as methyl, ethyl, and the like; amino, alkylamino, dialkylamino, aryloxy such as phenoxy, mercapto, alkylthio, alkylmercapto, disulfide (alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The electron donating or/and electron withdrawing groups may independently be present in any one of the substituents in Formula (I), (II) or/and (III) e.g., in R, $R_1$, $R_2$, $R_3$, $R_4$, $R_5$, $R_6$, $R'_6$, $R_7$, $R_8$, $R_9$ or/and $R_{10}$ as defined herein.

The at least one electron withdrawing or/and at least one electron donating group is preferably selected independently from halo, alkyl, alkenyl, alkynyl, nitro, carboxy, formyl, carboxyamido, aryl, quaternary ammonium, haloalkyl, aryl alkanoyl, hydroxy, alkoxy, carbalkoxy, amino, alkylamino, dialkylamino, aryloxy, mercapto, alkylthio, alkylmercapto, disulfide, alkanoyl, amino alkyl, aryloyl, cyano, sulfonyl, sulfoxide, heterocyclic, guanidine, sulfonium salts, mercaptoalkyl, and alkyldithio.

The term "sulfide" encompasses mercapto, mercapto alkyl and alkylthio, while the term disulfide encompasses alkyldithio.

In the compounds of the present invention, the at least one electron withdrawing or/and at least one electron donating group is more preferably selected independently from halo, alkyl, alkenyl, alkynyl, nitro, carboxy, formyl, carboxyamido, aryl, quaternary ammonium, haloalkyl, aryl alkanoyl, hydroxy, alkoxy, carbalkoxy, amino, alkylamino, dialkylamino, aryloxy, mercapto, alkylthio, alkylmercapto, and disulfide.

Even more preferably, the at least one electron withdrawing or/and at least one electron donating group is selected from halo, $C_1$-$C_6$-alkyl, $C_2$-$C_6$-alkenyl, $C_1$-$C_6$-alkynyl, nitro, carboxy, formyl, carboxyamido, $C_6$-$C_{10}$-aryl, quaternary ammonium, $C_1$-$C_6$-haloalkyl, $C_6$-$C_{10}$-aryl $C_2$-$C_6$-alkanoyl, hydroxy, $C_1$-$C_6$-alkoxy, $C_2$-$C_6$-carbalkoxy, amino, $C_1$-$C_6$-alkylamino, $C_1$-$C_6$-dialkylamino, $C_6$-$C_{10}$-aryloxy, mercapto, $C_1$-$C_6$-alkylthio, $C_1$-$C_6$-alkylmercapto, and disulfide.

Even more preferably, the electron withdrawing or/and electron donating groups may also be independently selected from halo, $C_1$-$C_6$-alkoxy, nitro, carboxy, formyl, carboxyamido, quaternary ammonium, hydroxy, amino, mercapto, and disulfide.

Most preferred electron withdrawing or/and electron donating groups are independently selected from halo such as fluoro and $C_1$-$C_6$-alkoxy such as methoxy and ethoxy.

The term "carbalkoxy" as used herein alone or in combination with other term(s) means an —CO—O-alkyl, wherein alkyl is as defined herein, taking into account that the —CO—O— group provides one carbon atom in addition to those of the alkyl group. The carbalkoxy group preferably contains from 2 to about 20 carbon atoms ($C_2$-$C_{20}$-carbalkoxy), more preferably from 2 to about 8 carbon atoms ($C_2$-$C_8$-carbalkoxy), even more preferably from 2 to about 6 carbon atoms ($C_2$-$C_6$-carbalkoxy), and most preferably from 2 to 3 carbon atoms ($C_2$-$C_3$-carbalkoxy).

The term "alkanoyl" as used herein alone or in combination with other term(s) means an alkanoyl group —CO-alkyl, wherein alkyl is as defined herein, taking into account that the —CO— group provides one carbon atom in addition to those of the alkyl group. The alkanoyl preferably contains from 2 to about 20 carbon atoms ($C_2$-$C_{20}$-alkanoyl), more preferably from 2 to about 8 carbon atoms ($C_2$-$C_8$-alkanoyl), even more preferably from 2 to about 6 carbon atoms ($C_2$-$C_6$-alkanoyl), and most preferably from 2 to 3 carbon atoms ($C_2$-$C_3$-alkanoyl). The alkanoyl group may be straight chained or branched. The alkanoyl groups include, for example, formyl, acetyl, propionyl, butyryl, isobutyryl, tertiary butyryl, pentanoyl and hexanoyl.

As employed herein, a heterocyclic group contains at least one heteroatom in the cyclic structure, preferably one, two, three or four heteroatoms. The at least one heteroatom may be independently selected from sulfur, nitrogen and oxygen. The heterocyclic groups contemplated by the present invention include heteroaromatics and saturated and partially saturated heterocyclic groups. The heterocyclics may be monocyclic, bicyclic, tricyclic or polycyclic and may be fused rings. The heterocyclics also include the so-called benzoheterocyclics. Heterocyclic groups may be unsubstituted or mono or polysubstituted with electron withdrawing or/and electron donating groups. The heterocyclic groups preferably contain up to 18 ring atoms and up to a total of 17 ring carbon atoms and may be unsubstituted or mono or polysubstituted with electron withdrawing or/and electron donating groups.

More preferably, the heterocyclic group may be independently selected from 5 or 6-membered monocyclic heterocyclic groups and may be unsubstituted or mono or polysubstituted with electron withdrawing or/and electron donating groups. The heterocyclic group may also be more preferably selected independently from furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Even more preferably, the heterocyclic moieties are those aforementioned heterocyclics which are monocyclic.

The heterocyclics may also be more preferably selected independently from thienyl, furyl, pyrrolyl, benzofuryl, benzothienyl, indolyl, oxazolyl, methylpyrrolyl, morpholinyl, pyridiyl, pyrazinyl, imidazolyl, pyrimidinyl, and pyridazinyl. Especially preferred heterocyclic are independently selected from furyl, oxazolyl, pyridyl, pyrazinyl, imidazolyl, pyrimidinyl, and pyridazinyl. The most preferred heterocyclics are independently selected from furyl, pyridyl and oxazolyl.

The monocyclic 5- or 6-membered heterocyclic groups in the compounds of the present invention are preferably of the Formula (IV):

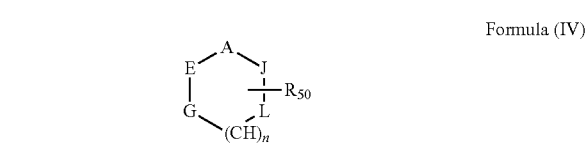

Formula (IV)

or those corresponding partially or fully saturated form thereof, wherein n is 0 or 1; and $R_{50}$ is H, an electron withdrawing group or an electron donating group;

A, E, L, J and G are independently CH, or a heteroatom selected from the group consisting of N, O, S; but when n is 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety.

If the ring depicted in Formula (IV) contains a nitrogen ring atom, then the N-oxide forms are also contemplated to be within the scope of the invention.

When $R_2$ or $R_3$ is a heterocyclic of Formula (IV), it may be bonded to the main chain by a ring carbon atom. When n is 0, $R_2$ or $R_3$ may additionally be bonded to the main chain by a nitrogen ring atom.

The term "heterocyclic alkyl" as used herein alone or in combination with other term(s) means an alkyl group as defined above carrying a heterocyclic substituent as defined above. Preferred heterocyclic alkyl groups are heterocyclic-$C_1$-$C_6$-alkyl, heterocyclic-$C_1$-$C_3$-alkyl, wherein the heterocyclic may be a preferred, more preferred or most preferred heterocyclic group as defined herein.

The term "alkyl heterocyclic" as used herein alone or in combination with other term(s) means a heterocyclic group as defined above carrying at least one alkyl substituent as defined above. Preferred alkyl heterocyclic groups are $C_1$-$C_6$-alkyl-heterocyclic, $C_1$-$C_3$-alkyl-heterocyclic, wherein the heterocyclic group may be a preferred, more preferred or most preferred heterocyclic group as defined herein.

The preferred compounds are those wherein n is 1, but di (n=2), tri (n=3) and tetrapeptides (n=4) are also contemplated to be within the scope of the invention.

In the ZY groups representative of $R_2$ or/and $R_3$, in the formula (I) or/and (II), Z may be O, S, $S(O)_a$, wherein a is 1-3, $NR_4$, $NR'_6$, $PR_4$ or a chemical bond; and Y may be hydrogen, alkyl, aryl, aryl alkyl, alkenyl, alkynyl, halo, heterocyclic, heterocyclic alkyl, alkyl heterocyclic, and Y may be unsubstituted or substituted with at least one electron donating group or/and at least one electron withdrawing group, provided that when Y is halo, Z is a chemical bond, or ZY taken together may be $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$ or $N^+R_5R_6R_7$,

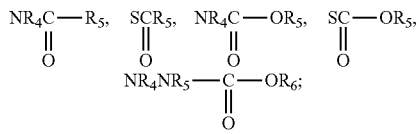

wherein $R_4$, $R_5$, $R'_6$, $R_6$, $R_7$, are as defined herein.

The ZY groups representative of $R_2$ or/and $R_3$ in the Formula (I) or/and (II) may be hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), alkoxy amino [(NHOR$_{18}$) wherein $R_{18}$ is alkyl], N-alkylhydroxylamino [(NR$_{18}$)OH wherein $R_{18}$ is alkyl], N-alkyl-O-alkylhydroxyamino, i.e., [N(R$_{18}$)OR$_{19}$ wherein $R_{18}$ and $R_{19}$ are independently alkyl], and O-hydroxylamino (—O—NH$_2$); alkylamido such as acetamido; trifluoroacetamido; alkoxyamino, (e.g., NH(OCH$_3$); and heterocyclicamino, such as pyrazoylamino.

In a preferred ZY group, Z is O, $NR_4$ or $PR_4$; Y is hydrogen or alkyl.

In another preferred embodiment,
ZY is $NR_4R_5R_7$, $NR_4OR_5$, $ONR_4R_7$,

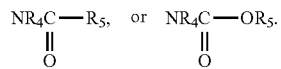

In a more preferred that ZY is $NR_4OR_5$, or $ONR_4R_7$.

Another more preferred ZY is N-hydroxyamino, N-alkylhydroxyamino, N-alkyl-O-alkyl hydroxyamino, O-alkylhydroxyamino, N-alkoxy-N-alkylamino, N-alkoxyamino, or N-carbalkoxy.

In Formula (I), R is preferably aryl or aryl alkyl, more preferably R is aryl alkyl, wherein R is unsubstituted or substituted with at least one electron donating group or/and at least one electron withdrawing group. R may be phenyl or benzyl, most preferably benzyl, wherein R is unsubstituted or substituted with at least one electron donating group or/and at least one electron withdrawing group. If R is substituted, R is preferably substituted on the aryl ring. In this embodiment, the at least one electron donating group or/and at least one electron withdrawing group is preferably halo, more preferably fluoro.

In Formulae (I), (II) or/and (III), $R_1$ is H or alkyl. More preferably, $R_1$ is alkyl, preferably containing from 1 to 6 carbon atoms, more preferably containing from 1 to 3 carbon atoms. Most preferably the $R_1$ group is methyl. $R_1$ may be unsubstituted or substituted with at least one electron donating group or/and at least one electron withdrawing group.

Further, it is preferred that one of $R_2$ and $R_3$ is hydrogen. It is more preferred that $R_2$ is hydrogen. Other preferred moieties of $R_2$ in Formula (I) are aryl such as phenyl, aryl alkyl such as benzyl, and alkyl. It is to be understood that the preferred groups of $R_2$ may be unsubstituted or mono or poly substituted with electron donating or/and electron withdrawing groups. It is preferred that the at least one electron withdrawing or/and at least one donating group in $R_2$ is independently alkoxy, N-hydroxyamino, N-alkylhydroxyamino, N-alkyl-O-alkyl hydroxyamino or O-alkylhydroxyamino, and especially methoxy or ethoxy.

In Formulae (I), (II) or/and (III), $R_3$ may be hydrogen, an alkyl group unsubstituted or substituted by at least an electron donating or/and at least one electron withdrawing group, an aryl group unsubstituted or substituted by at least an electron donating or/and at least one electron withdrawing group heterocyclic, heterocyclic alkyl, or ZY.

It is preferred that $R_3$ is hydrogen, alkyl unsubstituted or substituted by at least an electron donating or/and at least one electron withdrawing group, aryl which is unsubstituted or substituted by at least one electron donating group or/and at least one electron withdrawing group, heterocyclic, heterocyclic alkyl or ZY, wherein Z is O, $NR_4$ or $PR_4$; Y is hydrogen or alkyl; ZY is $NR_4NR_5R_7$, $NR_4OR_5$, $ONR_4R_7$,

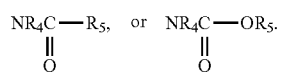

It is also preferred that $R_3$ is alkyl unsubstituted or substituted by at least an electron donating or/and at least one electron withdrawing group; or Z—Y, wherein Z—Y is as defined herein.

It is also preferred that $R_3$ is alkyl unsubstituted or substituted by at least an electron donating or/and at least one electron withdrawing group; $NR_4OR_5$, or $ONR_4R_7$, wherein $R_4$, $R_5$ and $R_7$ are as defined herein.

It is also preferred that $R_3$ is $CH_2$-Q, wherein Q is alkoxy especially containing 1-3 carbon atoms; or $R_3$ is $NR_4OR_5$ or $ONR_4R_7$, wherein $R_4$, $R_5$, and $R_7$ are as defined herein.

$R_3$ is also preferably alkyl which is unsubstituted or substituted with at least one alkoxy especially containing 1-3 carbon atoms.

$R_3$ is also preferably $CH_2$-Q, wherein Q is alkoxy preferably containing 1-3 carbon atoms, more preferably Q is ethoxy or methoxy.

$R_3$ is also preferably $NR_4OR_5$, or $ONR_4R_7$, wherein $R_4$, $R_5$ and $R_7$ are as defined herein, and $R_4$, $R_5$ and $R_7$ are as defined herein, e.g. N-alkoxy, N-alkoxy-N-alkylamino or N-carbalkoxy.

$R_3$ is also preferably heterocyclic, heterocyclic alkyl, or aryl, which may be unsubstituted or substituted with at least an electron donating or/and at least one electron withdrawing group. A most preferred heterocyclic in $R_3$ is furyl or oxazolyl.

$R_3$ is also preferably selected from the group consisting of hydrogen, alkyl, arylalkyl such as benzyl, alkoxy, alkoxyalkyl, aryl such as phenyl, heterocyclic, heterocyclic alkyl, N-alkoxy-N-alkylamino, N-alkoxyamino and N-carbalkoxy.

It is to be understood that the preferred groups of $R_3$ may be unsubstituted or mono or poly substituted with electron donating or/and electron withdrawing groups. It is preferred that the at least one electron withdrawing or/and at least one electron donating group in $R_3$ is independently alkoxy, N-hydroxyamino, N-alkylhydroxyamino, N-alkyl-O-alkyl hydroxyamino or O-alkylhydroxyamino, and especially methoxy or ethoxy.

$R_4$, $R_5$, $R_6$, $R'_6$, $R_7$ and $R_8$ are preferably independently hydrogen or alkyl.

$R_4$, $R_5$, and $R_7$ are preferably independently hydrogen or alkyl preferably containing 1-3 carbon atoms.

The most preferred aryl is phenyl. The most preferred halo is fluoro.

In the compounds of Formula (I), R is preferably aryl alkyl, wherein R is unsubstituted or substituted with at least one electron donating group or/and at least one electron withdrawing group.

In the compounds of Formula (I), $R_1$ is preferably alkyl which is unsubstituted or substituted with at least one electron donating group or/and at least one electron withdrawing group.

In the compounds of Formula (I), $R_2$ and $R_3$ is preferably independently hydrogen, alkyl which is unsubstituted or substituted by at least one electron donating group or/and at least one electron withdrawing group, aryl which is unsubstituted or substituted by at least one electron donating group or/and at least one electron withdrawing group, heterocyclic, heterocyclic aryl, or ZY; wherein Z is O, $NR_4$ or $PR_4$; and Y is hydrogen or alkyl; or ZY is $NR_4NR_5R_7$, $NR_4OR_5$, $ONR_4R_7$,

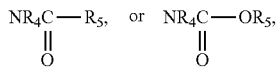

wherein $R_4$, $R_5$ and $R_7$ are as defined herein.

In the compounds of Formula (I), the preferred groups of $R_2$ and $R_3$ may be unsubstituted or mono or poly substituted with electron donating or/and electron withdrawing groups, such as alkoxy (e.g., methoxy, ethoxy, and the like), N-hydroxyamino, N-alkylhydroxyamino, N-alkyl-O-alkyl hydroxyamino and O-alkylhydroxyamino.

In the compounds of Formula (I), the at least one electron donating group or/and at least one electron withdrawing group in $R_2$ or/and $R_3$ is preferably independently hydroxy or alkoxy.

It is more preferred that in the compounds of Formula (I), $R_2$ is hydrogen.

In the compounds of Formula (II), $R_1$ is preferably methyl.

In preferred compounds of Formula (II), $R_3$ is hydrogen or alkyl unsubstituted or substituted by at least one electron donating group or/and at least one electron withdrawing group; or $R_3$ is heterocyclic, heterocyclic alkyl, or Z—Y, wherein Z—Y and heterocyclic are as defined herein.

In other preferred compounds of Formula (II), $R_3$ is an alkyl group which is unsubstituted or substituted by at least one electron donating group or/and at least one electron withdrawing group, $NR_4OR_5$ or $ONR_4R_7$, wherein $R_4$, $R_5$ and $R_7$ are as defined herein and wherein the at least one electron donating group or/and at least one electron withdrawing group is preferably selected from hydroxy and alkoxy.

In further preferred compounds of Formula (II), $R_3$ is $CH_2$-Q, wherein Q is alkoxy preferably containing 1-3 carbon atoms, more preferably methoxy, or $R_3$ is $NR_4OR_5$ or $ONR_4R_7$ wherein $R_4$, $R_5$ and $R_7$ are independently hydrogen or alkyl containing 1-3 carbon atoms.

In other preferred compounds of Formula (II), $R_3$ is —$CH_2$-Q, wherein Q is alkoxy containing 1 to 3 carbon atoms.

In the compounds of Formula (II), Ar is preferably phenyl unsubstituted or substituted with at least one halo, preferably with at least one fluoro. More preferably Ar in Formula (II) is unsubstituted phenyl.

In preferred compounds of Formula (III), $R_9$ is hydrogen or fluoro, $R_3$ is selected from the group consisting of methoxymethyl, phenyl, N-methoxy-N-methylamino, and N-methoxyamino, and $R_1$ is methyl.

The most preferred compounds of the present invention include:
(R)-2-acetamido-N-benzyl-3-methoxy-propionamide;
(R)-2-acetamido-N-benzyl-3-ethoxy-propionamide;
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide;
D-α-acetamido-N-(2-fluorobenzyl)-2-furanacetamide;
D-α-acetamido-N-(3-fluorobenzyl)-2-furanacetamide.

It is to be understood that the Markush groups of $R_1$, $R_2$, $R_3$, R and n as described herein can be combined and permutated. The various combinations and permutations not explicitly disclosed herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

More preferred is a compound of Formula (I), (II) or/and (III) in the R configuration, preferably substantially enantiopure, wherein the substituent R is benzyl which is unsubstituted with at least one halo group, wherein $R_3$ is $CH_2$-Q, wherein Q is alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of compounds utilized in the present invention is described in U.S. Pat. Nos. 5,378,729 and 5,773,475, and in the international application PCT/EP 2005/010603 the contents of which are incorporated by reference.

The compounds utilized in the present invention are useful as such as depicted in the Formulae (I), (II) or/and (III) or can be employed in the form of salts in view of its basic nature by the presence of the free amino group. Thus, the compounds of Formulae (I), (II) or/and (III) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The physician will determine the dosage of the present therapeutic combinations which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the combinations and increase the dosage by small increments until the optimum effect under the circumstances is reached. When the composition is administered orally, larger quantities of the active agent will be required to produce the same effect as a smaller quantity given parenterally. The combinations of the present invention are useful in the same manner as comparable therapeutic agents and the dosage level is of the same order of magnitude as is generally employed with these other therapeutic agents.

In a preferred embodiment, the compounds (a) of the present invention is administered in amounts ranging from about 1 mg to about 100 mg per kilogram of body weight per day, more preferably in amounts ranging from about 1 mg to about 10 mg per kilogram of body weight per day. This dosage regimen may be adjusted by the physician to provide the optimum therapeutic response. Patients in need thereof may be treated with doses of the compound (a) of the present invention of at least 50 mg/day, preferably of at least 200 mg/day, more preferably of at least 300 mg/day, still more preferably of at least 400 mg/day and most preferably of at least 600 mg/day. Generally, a patient in need thereof may be treated with doses at a maximum of 6 g/day, more preferably a maximum of 1 g/day, still more a maximum of 800 mg/day, and most preferably a maximum of 600 mg/day. In some cases, however, higher or lower doses may be needed.

In a further preferred embodiment, the compound (b) of the present invention is administered in amounts ranging from about 100 mg/day to about 4 g/day.

In another preferred embodiment, the daily doses are increased until a predetermined daily dose is reached which is maintained during the further treatment.

In yet another preferred embodiment, several divided doses may be administered daily. For example, three doses per day may be administered, preferably two doses per day. It is more preferred to administer a single dose per day.

In yet another preferred embodiment, an amount of the compounds (a) of the present invention may be administered which results in a plasma concentration of 0.1 to 15 µg/ml (trough) and 5 to 18.5 µg/ml (peak), calculated as an average over a plurality of treated subjects, intravenous administration in emergency treatment might result in peak plasmid levels of up to 30 µg/ml.

The combinations of compounds of Formulae (I), (II) or/and (III) and compound (b) may be administered in a convenient manner, such as by oral, intravenous (where water soluble), intramuscular, intrathecal, rectal (e.g. suppository, gel, liquid, etc.) or subcutaneous routes. Oral, rectal or/and i.v. administration is preferred. In emergency treatment, i.v. administration is most preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

The combinations of compounds of Formulae (I), (II) or/and (III) and compound (b) may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the combinations of compounds of Formulae (I), (II) or/and (III) and compound (b) may be incorporated with excipients and used in the form of ingestible tablets, buccal tablets, troches, capsules, elixirs, suspensions, syrups, wafers, and the like. Such compositions and preparations should contain at least 1% of active compound of Formulae (I), (II) or/and (III). The percentage of the compositions and preparations may, of course, be varied and may conveniently be between about 5 to about 80% of the weight of the unit. The amount of combinations of compounds of Formulae (I), (II) or/and (III) and compound (b) in such therapeutically useful compositions is such that a suitable dosage will be obtained. Preferred compositions or preparations according to the present invention contains between about 10 mg and 6 g active compound of Formulae (I), (II) or/and (III).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compounds, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The pharmaceutical composition may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of preparing sterile powders for the manufacture of sterile injectable solutions, the preferred methods of preparation are vacuum drying, or freeze-drying optionally together with any additional desired ingredient.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredients are compounded for convenient and effective administration in effective amounts with a suitable pharmaceutically acceptable carrier in dosage unit form as hereinbefore described. A unit dosage form can, for example, contain the principal active compound (a) in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition, to curing or alleviating the patient's disease or condition.

The compounds of the present invention are administered to a patient suffering from the aforementioned type of disorder in an effective amount. These amounts are equivalent to the therapeutically effective amounts described hereinabove.

The present invention is further illustrated by the following example and figures.

BRIEF DESCRIPTION OF DRAWINGS

FIG. 9: Isobolographic characterization of the interaction between LCM and various AEDs in the 6 Hz seizures tests in mice.

FIG. 10: The effects of various AEDs administered alone and in combination with lacosamide on motor coordination in the rotarod test in mice. The results of the rotarod test are expressed as a percentage of animals showing motor co-ordination impairment. Each group consisted of 10 animals.

Figure 1:
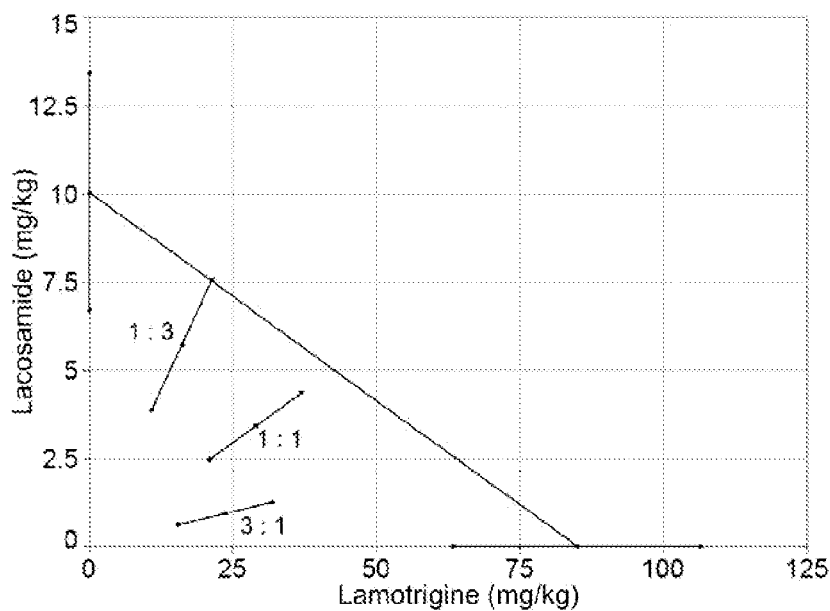
FIG. 1: Isobologram showing interactions between Lamotrigine and Lacosamide for three fixed-ratio combinations in the 6 Hz induced seizure model in mice. Median effective dose (ED50) values for LTG and LCM are placed on the X- and Y-axes, respectively. The straight line connecting these both ED50 values represents the theoretic line of additivity for a continuum of different fixed-dose ratios. The solid points depict the experimentally derived ED50mix values (with 95% confidence limits as the error bars) for total dose expressed as the proportion of LTG and LCM that produce a 50% effect.

For the testing of each AED alone at its $ED_{50}$, each group consisted of 20 animals. The Fisher's exact test was used for statistical comparisons.

FIG. 11: Summary of combined interaction results for anticonvulsant drug pairs obtained in 6 Hz-induced seizures model in mice.

FIG. 12: Profile of anticonvulsant activity and minimal toxicity of lacosamide in mice and rats FIG. 13: Profile of anticonvulsant activity and minimal toxicity of prototype anticonvulsants in mice and rats
MES=maximal electroshock, Sc=subcutaneous, Met=Metrazol/Chemoconvulsant, Bic=Bicucullin/Chemoconvulsant, Pic=Picrotoxin/Chemoconvulsant, AGS=audiogenic seizures.

EXAMPLE

The aim of this study was to investigate potential interactions between LCM and conventional AEDs (phenyloin (PHT), carbamazepine (CBZ), valproate (VPA), lamotrigine (LTG) or between LCM and novel AEDs, topiramate (TPM), gabapentin (GBP) or levetiracetam (LEV)) in the 6 Hz seizure model in mice using the isobolographic analysis. According to Deckers et al. (2000) an isobolographic method used to evaluate interactions among AEDs is considered to be the optimal method for detecting synergy, additivity or antagonism among AEDs in animal models of epilepsy. The adverse effects of such combinations were evaluated in the rotarod test.

Animals

The experiments were performed on adult male CBA mice (University Odessa) weighing between 20 and 28 g. The mice were kept in colony cages with free access to food and water, under standard laboratory conditions with natural light-dark cycle. After 1 week adaptation to laboratory conditions, the animals were randomly assigned to experimental groups consisting of ten mice. Each mouse was used only once. All experiments were performed between 9 am and 4 pm. Procedures involving animals and their care were conducted in accordance with current European Community regulations.

Drugs

The following AEDs were used in this study: LCM, LTG, VPA, CBZ, PHT, LEV, TPM, GBP donated by SCHWARZ Pharma. All drugs were dissolved in 0.5% methylcellulose and administered intraperitoneally (i. p.) in a volume of 0.2 ml/20 g body weight (CBZ, VPA—15 min; LCM, LTG—30 min; LEV, GBP—60 min; PHT, TPM—120 min before the test).

Fresh drug solutions were prepared ex tempore on each day of experimentation. These pretreatment times before testing of AEDs were based on information about their biologic activity from the literature (Barton et al., 2001; Luszczki et al., 2006).

6 Hz Seizure Test

"Psychomotor" seizures were induced via corneal stimulation (6 Hz, 32 mA, 0.2 ms rectangular pulse width, 3 s duration) using a Grass S48 stimulator (Barton et al., 2001).

At the time of drug administration, a drop of 0.5% tetracaine was applied to the eyes of all animals. Prior to the placement of corneal electrodes a drop of 0.9% saline was placed on the eyes. Animals were manually restrained and released immediately following the stimulation and observed for the presence or absence of seizure activity, being characterized by stun, forelimb clonus twitching of the vibrissae and Straub-tail. Protection was defined as the absence of a seizure (Barton et al., 2001). In control groups (with vehicle injection) all animals exhibited seizures. The protective efficacy of AEDs was determined as their ability to protect 50% of mice against 6 Hz seizure and expressed as respective median effective dose (ED50) values. To evaluate each ED50 value, at least four groups of 10 mice, after receiving progressive doses of an AED, were challenged with 6 Hz seizure. ED50 values (with 95% confidence limits) were calculated by computer probit analysis (Litchfield, Wilcoxon, 1949) and subsequently transformed into standard errors of mean (SEM).

Rotarod Test

The impaired motor function was quantified by the rotarod test in mice according to Dunham and Miya (1957). The rotarod test was undertaken by use of a rod of 3 cm diameter, rotating at constant speed of 6 rpm. In this test, an acute neurological deficit (adverse effects produced by AEDs) was indicated by the inability of the animals to maintain their equilibrium for at least 120 s on the rotating rod. The dose ratio assessed in this model was always 1:1. For comparison, each AED was tested alone at its ED50 and 50% of its ED50 in the 6 Hz model.

Data Analysis

The isobolographic analysis is based on a comparison of equieffective drug doses. In the present study, interactions between drugs, as regards their anticonvulsant efficacy against 6 Hz seizure test were evaluated isobolographically according to the procedure elaborated by Tallarida (1992); Porreca et al. (1990); Luszczki et al. (2006). The experimental (EDmix) and theoretical additive (EDadd) were determined from the dose-response curves of combined drugs (Tallarida et al., 1997). ED50 is defined as a dose of a drug protecting 50% of the animals against 6 Hz-induced seizures. ED50mix is an experimentally determined total dose of the mixture of two component drugs, which were administered in the fixed-ratio combination sufficient for a 50% protective effect. Conversely, ED50add represents a total additive dose of two drugs (calculated from the line of additivity), theoretically providing 50% protection against seizures. The respective 95% confidence limits of EDmix were calculated according to Litchfield and Wilcoxon (1949), and these of EDadd according to Tallarida and Murray (1987), and subsequently transformed to SEM, according to a procedure described in detail by Luszczki, et al. (2003).

To estimate the types of interactions, three fixed-dose ratios of the drugs were examined as follows 1:3, 1:1, and 3:1 in the 6 Hz-induced seizures. To visualize the types of interactions between LCM and AEDs studied, the isoboles were drawn by plotting the points reflecting the respective doses of LCM (on Y-axis) and doses of an AED on the X-axis. The straight line connecting ED50 values for the two tested drugs administered alone against 6 Hz-induces seizures, represents the theoretic isobole for additivity. If experimentally determined data points, reflecting the combinations of various fixed ratios, lie on this line the drug effects are additive (no interaction). If the points fall significantly below the additive line, the two component drugs act synergistically. Conversely, antagonism may be recognized if these points are localized above the additive isobole.

Moreover, an interaction index for various fixed-ratio combinations of two AEDs in the 6 Hz-test was calculated as a ratio ED50mix/ED50add. This ratio seems to be a good describer of the strength of interaction between two AEDs in isobolographic analysis (Luszczki et al., 2003; Berenbaum, 1989; Tallarida et al., 1999; Tallarida, 2001, 2002). If the index is smaller than 0.7, this indicates a synergistic effect. If the index is larger than 1.3, this indicate an antagonistic effect, and if the index is in between this indicates purely additive interaction (Luszczki et al., 2003; Kerry et al., 1975; Bourgeois, Wad, 1984, 1988; Bourgeois, 1988).

A protective index (PI) can be calculated by dividing a given TD50, obtained in the rotorod test, by the respective ED50 determined in the 6 Hz seizure test. The PI is considered a satisfactory margin of safety between AED doses and doses of AEDs exerting sedative, ataxic, or other neurotoxic side effects (Loscher, W., Nolting, B. The role of technical, biological and pharmacological factors in the laboratory evaluation of anticonvulsant drugs. IV. Protective indices, Epilepsy Res (1991), 9:1-10).

A benefit index (BI) is defined as a quotient of $PI_{mix}$ and $PI_{add}$ of respective fixed-ratio combinations, obtained directly from the isobolographic analysis. $PI_{mix}$ is a protective index experimentally determined, and $PI_{add}$ is a protective index theoretically calculated from the lines of additivity in the 6 Hz seizure and the rotorod test. BI unequivocally estimates advantages of the combination of two drugs applied in various fixed-ratio combinations. Moreover, BI provides the rationale for combining the respective AEDs in clinical practice if its value is >1.3, whereas BI<0.7 indicates unfavourable combinations of AEDs (Luszczki J J, Borowicz K K, Swiader M, Czuczwar S J, Interactions between oxcarbazepine and conventional antiepileptic drugs in the maximal electroshock test in mice: an isobolographic analysis, Epilepsia (2003), 44:489-99).

Results

1. AED Anticonvulsant Effects Against 6 Hz-Induced Seizures in Mice.

All studied AEDs (LCM, LTG, VPA, CBZ, PHT, LEV, TPM, GBP) produced dose-dependent anticonvulsant effects against 6 Hz seizure in mice. The ED50 values for the drugs administered alone are presented in FIG. 8.

Among the drugs lacosamide displayed the highest potency (i.e. lowest ED50).

2. Isobolographic Analysis of Interactions Between LCM and Numerous AEDs in the 6 Hz—Seizure Model.

Based on ED50 values determined for each AED individually, a theoretical additive ED50 for drug mixtures (ED50add values) was calculated for three fixed-ratios (1:3, 1:1 and 3:1). Subsequently, the experimental ED50mix values were determined for the same fixed-ratio combinations in the 6 Hz seizure test (FIG. 9). The isobolographic analysis demonstrated additive interactions between LCM+PHT (FIG. 4) and LCM+VPA (FIG. 2) in all fixed-ratio combinations (a non-significant synergistic effect, as the ED50mix is only slightly smaller than the ED50add). The combinations of LCM with LTG (FIG. 1), TPM (FIG. 6) and GBP (FIG. 7) exerted additive interactions for low doses of the test AED combined with high doses of LCM (i.e. at a fixed ratio of 1:3). For the 1:1 ratios synergistic effects were observed between LCM and LTG, TPM or GBP, respectively. Similarly, synergistic interactions were noted for high doses of LTG, TPM or GBP, respectively, combined with a low doses of LCM (i.e. fixed ratio of 3:1; FIG. 9). Interaction between LCM+CBZ (FIG. 3) and LCM+LEV (FIG. 5) were synergistic across all ratios (FIG. 9), since interaction indices for these combinations were lower than 0.7 (FIG. 9).

3. Rotarod Test

Detailed results are shown in FIG. 10. LCM co-administered with other AEDs in the dose ratio of 1:1 in no case did produce significant impairment of motor performance in mice.

FIG. 11 summarizes the types of interactions observed between 7 drug pairs with respect to 6 Hz-induced seizures test.

Discussion

Figures 7, 8:
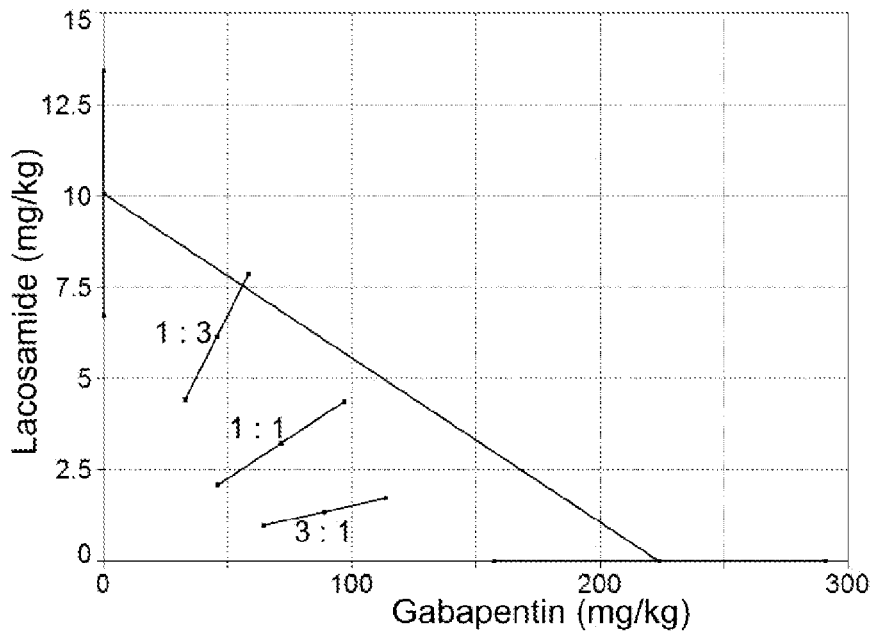
FIG. 7: Interactions between Gabapentin and Lacosamide (see details in FIG. 1)
FIG. 8: Effects of LCM and conventional antiepileptic drugs against 6 Hz seizure in mice. Confidence limits are indicated in brackets.

This study demonstrates that LCM fully protected mice from 6 Hz psychomotor seizures with an ED50 of 10.1 mg/kg. This dose corresponds well with the ED50 (9.9 mg/kg) determined in the anticonvulsant drug screening program of NINDS but is 2-3 times higher than the ED50 needed for protection of maximal electroshock seizures in mice and rats (Stoehr et al., submitted). Furthermore, the antiseizure effect of various AEDs (LTG, CBZ, PHT, TPM, GBP; FIG. 8) occurred at significantly higher doses than those needed for suppression of seizures in the MES test obtained in other studies. In general our data are in agreement with those reported by Barton et al. (2001). Lacosamide is the drug with the highest potency in this model when compared to the other tested AEDs. In contrast to the sodium channel modulators phenyloin, lamotrigine and carbamazepine it did not impair rotarod performance at pharmacological doses.

The 6 Hz test is regarded a model for treatment resistant seizures e.g. due to the observation that LEV provides complete protection in this model despite being inactive in a variety of other models (Gower et al., 1993; Klitgaard et al., 1998; Löscher, Honack, 1993; Patsalos, 2004). Our data confirm the differences in the pharmacological profile of the MES and 6 Hz seizure models. Barton et al. (2001) used the immediate early gene c-Fos as a marker of seizure induced neuronal activation and showed that 6 Hz induced seizures result in a clearly different pattern of neuronal activation than that observed following maximal electroshock or PTZ induced seizures. Duncan and Kohn (2004) showed by using the 2-deoxy glucose technique that this specific pattern of neuronal activation was attenuated by lacosamide while the drug had no effect on basal patterns.

Figure 2:
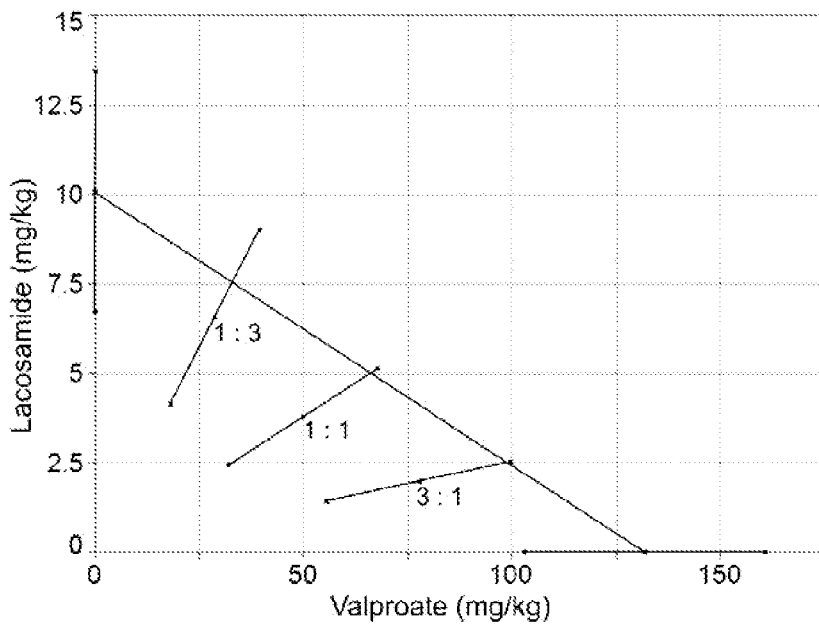
FIG. 2: Interactions between Valproate and Lacosamide (see details in FIG. 1)
Figure 3:
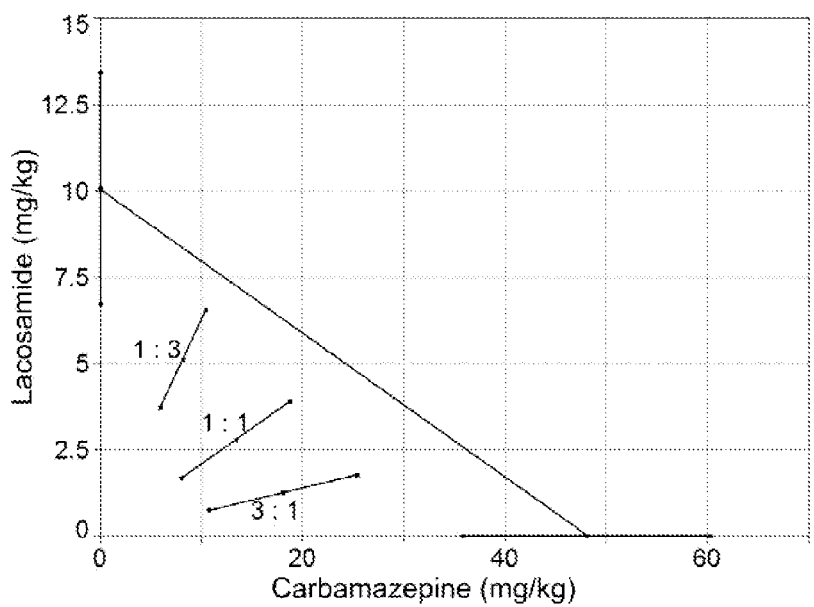
FIG. 3: Interactions between Carbamazepine and Lacosamide (see details in FIG. 1)
Figure 4:
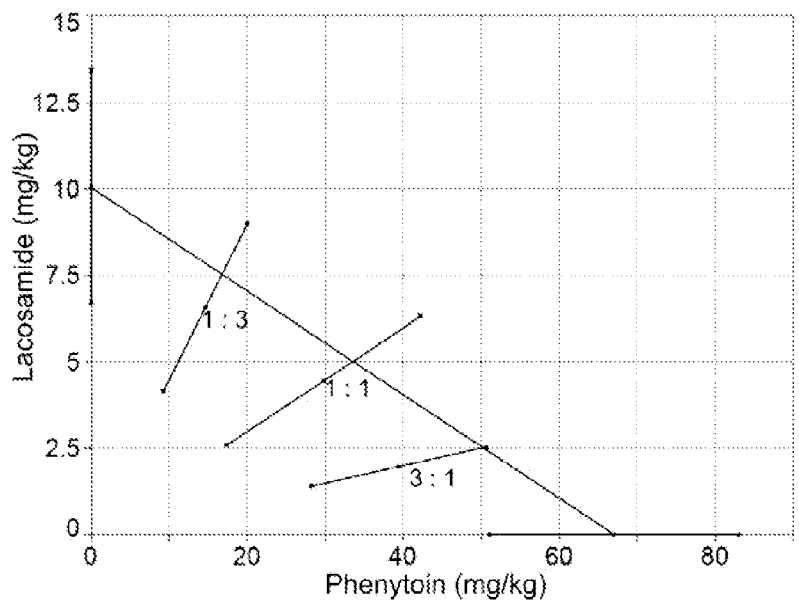
FIG. 4: Interactions between Phenyloin and Lacosamide (see details in FIG. 1)
Figure 5:
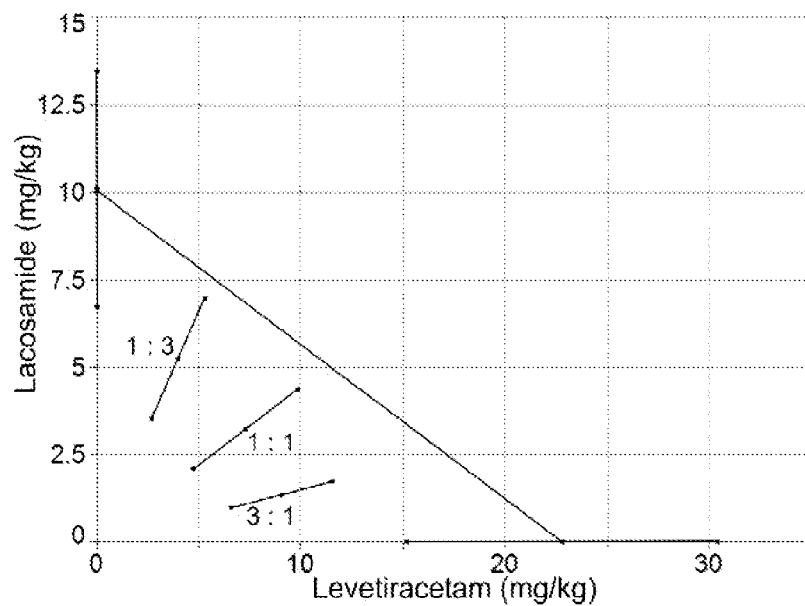
FIG. 5: Interactions between Levetiracetam and Lacosamide (see details in FIG. 1)
Figure 6:
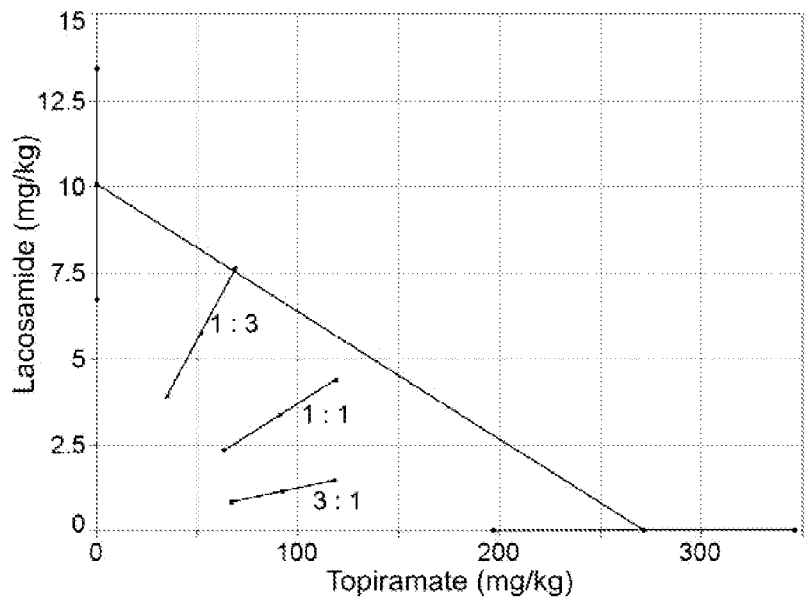
FIG. 6: Interactions between Topiramate and Lacosamide (see details in FIG. 1)

The isobolographic analysis revealed that LCM acts synergistically with LEV and CBZ across all examined fixed ratios. LTG, TPM and GBP in combination with LCM (at the fixed ratios of 1:1 and 3:1) were similarly associated with synergistic interactions and showed tendency towards synergistic interactions at fixed ratios of 1:3 (FIG. 1, FIG. 6 and FIG. 7). Additionally, it was found that the interactions between LCM and VPA or PHT were additive for protection against 6 Hz-induced seizures (FIG. 2, FIG. 4).

None of the drug combinations studied exhibited infraadditive effects (antagonism between drugs for antiseizure efficacy) or potentiation of toxicities. In no cases in which there was potentiation of antiseizure activities there was also potentiation of acute neurotoxicities. This is, of course, a desirable interaction for any drug combination since the result is an improved margin of safety.

It is of interest to note that in general a combination of low dose lacosamide with a high dose of another AED yielded higher levels of synergism as vice versa. This and the fact that lacosamide acted at least additively with all other tested AEDs makes it an ideal add-on drug for the therapy of treatment resistant seizures.

We can suggest some mechanism underlying the different types of interactions observed between LCM and other AEDs. First of all one can exclude pharmacokinetic effects as the reason for the additive or synergistic effects although plasma levels of AEDs have not been determined. LCM does not inhibit or induce a large variety of drug metabolizing enzymes, nor is it metabolized to a significant extent by one of them. Additionally, clinical population pharmacokinetic analysis provided no evidence for any effect of LCM on plasma levels of AEDs or vice versa. Thus the interactions found in the present study are purely of pharmacodynamic nature.

The mechanisms of action underlying the nature of the synergistic or additive interaction between LCM and tested AEDs are unknown. According to Deckers et al. (2000), synergistic interactions are likely between drugs with different mechanisms of action, and additivity may be expected for drugs sharing similar mechanisms.

From the analysis of the adverse activity in the rotarod test it may be postulated that the combinations displaying clearcut synergy or additivity in the 6 Hz seizure test didn't associate with impairment of motor coordination in mice.

It should be emphasized that the dose ratio may be critical for the final outcome of type of an interaction between AEDs. This is evident from the present result that in some dose ratios, the interactions were simply additive (e.g. LCM+GBP, 1:3) and in other dose ratios were therapeutically synergistic. Results from other studies also point to this problem (Gordon et al., 1993; Borowicz et al., 2000). For instance, Borowicz et al. (2002) by using the MES test in mice it has been observed that GBP in combination with CBZ showed an additive interaction at a dose ratio of 1:1 but for many others very significant synergistic interactions. From this point of view this must be considered by the clinicians when introducing drug combinations in epilepsy patients.

Theoretically, a drug combination showing only additivity for anticonvulsant actions but not or minimal adverse effects, also is relevant from a clinical point of view (Luszczki et al., 2003), since combinations of low doses can provide the same antiseizure effect while having diminished side effects.

It is concluded that the compounds of the Formulae (I), (II) or/and (III) exhibit a synergistic effect together with an AED different from the compound of Formulae (I), (II) or/and (III) in the prevention, alleviation or/and treatment of epileptic seizures.

REFERENCES

Barton, M. E., Klein, B. D., Wolf, H. H., White, H. S, Pharmacological characterization of the 6 Hz psychomotor seizure model of partial epilepsy, Epilepsy Res., 47 (2001), pp. 217-227.

Berenbaum, M. C., What is synergy? Pharmacol Rev, 41 (1989), pp. 93-141.

Bialer, M., Johannessen, S. I., Kupferberg, H. J., Levy, R. H., Loiseau, P., Perucca, E., Progress report on new antiepileptic drugs: a summary of the Fifth Eilat Conference (EILAT V), Epilepsy Research, 43 (2001), pp. 11-58.

Bialer, M., Johannessen, S. I., Kupferberg, H. J., Levy, R. H., Loiseau, P., Perucca, E., Progress report on new antiepileptic drugs: a summary of the Sixth Eilat Conference (EILAT VI), Epilepsy Research, 51 (2002), pp. 31-71.

Bialer, M., Johannessen, S. I., Kupferberg, H. J., Levy, R. H., Perucca, E., Torbjom, T., Progress report on new antiepileptic drugs: a summary of the Seventh Eilat Conference (EILAT VII), Epilepsy Research, 61 (2004), pp. 1-48.

Borowicz, K. K., Kleinrok, Z., Czuczwar, S. J., The AMPA/kainate receptor antagonist, LY 300164, increases the anticonvulsant effects of diazepam, Naunyn Schmiedebergs Arch Pharmacol (2000), 361:629-35.

Borowicz, K. K., Swiader, M., Luszczki, J., Czuczwar, S. J., Effect of gabapentin on the anticonvulsant activity of antiepileptic drugs against electroconvulsions in mice: an isobolographic analysis, Epilepsia, 43 (2002), pp. 956-963.

Bourgeois, B. F. D., Anticonvulsant potency and neurotoxicity of valproate alone and in combination with carbamazepine and phenobarbital, Clin Neuropharmacol (1988), 11:348-59.

Bourgeois, B. F. D., Wad, N., Combined administration of carbamazepine and phenobarbital: effect on anticonvulsant activity and neurotoxicity, Epilepsia (1988), 29:482-7.

Brodie, M. J., Do we need any more new antiepileptic drugs? Epilepsy Res, 45 (2001), 3-6.

Deckers, C. L. P., Czuczwar, S. J., Hekster, Y. A., et al., Selection of antiepileptic drug polytherapy based on mechanisms of action: the evidence reviewed, Epilepsia, 41 (2000), pp. 1364-1374.

Dunham, N. W., Miya, T. S., A note on a simple apparatus for detecting neurological deficit in rats and mice, J. Am. Pharm. Assoc. 46 (1957), pp. 208-209.

Gower, A. J., Noyer, M., Verloes, R., et al., Ucb L059, a novel anticonvulsant drug: pharmacological profile in animals, Eur J Pharmacol 222 (1992), pp. 193-203; Erratum published in: Eur J Pharmacol (1993), 230:389.

Hovinga, C. A., Erlosamide Schwarz Pharma, IDrugs 6 (Suppl. 5, 2003).

Kerry, D. W., Hamilton-Miller, J. M. T., Brumfitt, W., Trimethoprim and rifampicin: in vitro activities separately and in combination, J Antimicrob Chemother (1975), 1:417-27.

Klitgaard, H., Matagne, A., Gobert, J., et al., Evidence for a unique profile of levetiracetam in rodent models of seizures and epilepsy, Eur J Pharmacol, 353 (1998), pp. 191-206.

Kramer, G., The limitations of antiepileptic drug monotherapy. Epilepsia, 38 (Suppl. 5, 1997), S9-S13.

Litchfield, J. T., Wilcoxon, F., A simplified method of evaluating dose-effect experiments, J. Pharmacol Exp Ther 96 (1949), pp. 99-113.

Loiseau, P., DO we need novel anti-epileptic drugs? Br. J. Clin. Pract., 42 (1988) 2-3.

Löscher, W., Honack, D., Profile of ucb L059, a novel anticonvulsant drug, in models of partial and generalized epilepsy in mice and rats, Eur J Pharmacol, 232 (1993), pp. 147-158.

Löscher, W., Nolting, B., The role of technical, biological and pharmacological factors in the laboratory evaluation of anticonvulsant drugs. IV. Protective indices, Epilepsy Res (1991), 9:1-10

Luszczki, J. J., Andres, M. M., Czuczwar, P., Cioczek-Czuczwar, A., Ratnaraj, N., Patsalos, P. N. and Czuczwar S. J., Pharmacodynamic and pharmacokinetic characterization of interactions between Levetiracetam and numerous antiepileptic drugs in the mouse maximal electroshock seizure model: an isobolographical analysis, Epilepsia, 47 (2006), pp. 10-20.

Luszczki, J. J., Czuczwar, M., K is, J., Krysa, J., Pasztelan, I., Swiader, M. and Czuczwar, S. J., Interactions of lamotrigine with topiramate and first-generation antiepileptic drugs in the maximal electroshock test in mice: an isobolographic analysis, Epilepsia, 44 (8), (2003) pp. 1003-1013.

Luszczki J J, Borowicz K K, Swiader M, Czuczwar S J, Interactions between oxcarbazepine and conventional antiepileptic drugs in the maximal electroshock test in mice: an isobolographic analysis, Epilepsia (2003), 44:489-99

Luszczki, J. J., Czuczwar, S. J., Isobolographic and subthreshold methods in the detection of interactions between oxcarbazepine and conventional antiepileptics—a comparative study, Epilepsy Res., 56 (2003), pp. 27-42.

Patsalos, P. N., Levetiracetam: pharmacology and therapeutics in the treatment of epilepsy and other neurological conditions, Rev Contemp Pharmacother, 13 (2004), pp. 1-168.

Porreca, F., Jiang, Q., Tallarida, R. J., Modulation of morphine antinociception by peripheral [Leu5] enkephalin: a synergistic interaction, Eur J Pharmacol, 179 (1990), pp. 463-468.

Sander, J. W. A. S, and Shorvon, S. D., Incidence and prevalence studies in epilepsy and their methodological problems: a review, J. Neurol. Neurosurg. Phychiat., 50 (1987) 829-839.

Schmidt, D. and Morselli, P. L. (Eds.), Intractable Epilepsy: Experimental and Clinical Aspects, Raven Press, New York, N.Y. (1986).

Tallarida, R. J., Statistical analysis of drug combinations for synergism, Pain (1992), 49:93-7.

Tallarida, R. J., Stone, D. J., McCary, J. D., et al., Response surface analysis of synergism between morphine and clonidine, J Pharmacol Exp Ther (1999), 289:8-13.

Tallarida, R. J., Stone, D. J., Raffa, R. B., Efficient designs for studying synergistic drug combinations, Life Sci (1997), 61:PL417-25.

Tallarida, R. J., The interaction index: a measure of drug synergism, Pain (2002), 98:163-8.

Warner, T., Patsalos, P. N., Prevett, M., et al., Lamotrigine-induced carbamazepine toxicity: an interaction with carbamazepine-10,11-epoxide, Epilepsy Res (1992), 11:147-50.

The invention claimed is:

1. A method for alleviating and/or treating epileptic seizures in a subject, the method comprising administering to the subject (a) lacosamide and/or a pharmaceutically acceptable salt thereof; and (b) levetiracetam and/or a pharmaceutically acceptable salt thereof, optionally together with a pharmaceutically acceptable carrier, diluent and/or adjuvant, wherein (a) lacosamide and (b) levetiracetam are in a fixed-dose ratio of about three parts lacosamide to at least about one part levetiracetam calculated on the $ED_{50}$ values of the individual components (a) and (b), and wherein (a) and (b) are in separate dosage forms which are separately packaged but are co-marketed or co-promoted for use in combination with each other.

2. The method of claim 1, wherein the separate dosage forms are sold independently of one another.

3. The method of claim 1, wherein the separate dosages forms are co-presented in separate packaging.

4. The method of claim 1 further comprising administering the separate dosage forms simultaneously or subsequently.

5. The method of claim 1 further comprising administering the separate dosage forms by the same or by different routes.

6. The method of claim 1, wherein (a) lacosamide and (b) levetiracetam are in a fixed-dose ratio of lacosamide: levetiracetam of between about 3:1 to about 1:6, calculated on the $ED_{50}$ values of the individual components (a) and (b).

7. The method of claim 1, wherein (a) lacosamide and (b) levetiracetam are in a fixed-dose ratio of lacosamide: levetiracetam of between about 3:1 to about 1:3, calculated on the $ED_{50}$ values of the individual components (a) and (b).

8. The method of claim 1, wherein (a) lacosamide and (b) levetiracetam are in a fixed-dose ratio of lacosamide: levetiracetam of between about 1:1 to about 1:3, calculated on the $ED_{50}$ values of the individual components (a) and (b).

9. The method of claim 1, wherein (a) lacosamide and (b) levetiracetam are in a fixed-dose ratio of lacosamide: levetiracetam of about 1:2, calculated on the $ED_{50}$ values of the individual components (a) and (b).

10. The method of claim 1, wherein (a) lacosamide and (b) levetiracetam are in a fixed-dose ratio of lacosamide: levetiracetam of about 1:4, calculated on the $ED_{50}$ values of the individual components (a) and (b).

11. The method of claim 1, wherein (a) lacosamide and (b) levetiracetam are in a fixed-dose ratio of lacosamide: levetiracetam of about 1:5, calculated on the $ED_{50}$ values of the individual components (a) and (b).

12. The method of claim 1, wherein the $ED_{50}$ value of lacosamide is at least about 0.5 mg/kg up to about 30 mg/kg and the $ED_{50}$ values of levetiracetam is at least about 10 mg/kg up to about 100 mg/kg.

13. The method of claim 1, wherein the $ED_{50}$ value of lacosamide is 10. 1 mg/kg and the $ED_{50}$ value of levetiracetam is 22.8 mg/kg.

14. The method of claim 1 comprising administering to the subject levetiracetam in a dose of at least 1000 mg/day up to 3000 mg/day and lacosamide in a dose of at least 100 mg/day, and at a maximum of 600 mg/day.

15. The method of claim 1, wherein the epileptic seizures are selected from the group consisting of partial seizures with and without secondary generalization; primarily generalized seizures; and status epilepticus.

16. The method of claim 14, wherein the epileptic seizures are partial seizures with and without secondary generalization.

17. The method of claim 1 comprising administering (a) lacosamide and (b) levetiracetam as three doses per day, two doses per day, or as a single dose per day.

18. The method of claim 5 comprising administering the separate dosage forms orally and/or intravenously.

19. The method of claim 17 comprising administering at least one of the separate dosage forms orally in the form of a hard shell gelatin capsule; a soft shell gelatin capsule; or a tablet.

20. The method of claim 1 comprising administering lacosamide and/or a pharmaceutically acceptable salt thereof and levetiracetam and/or a pharmaceutically acceptable salt thereof in amounts to provide a therapeutic effect in alleviating and/or treating epileptic seizures that is greater than additive of the therapeutic effect of the compounds administered alone.

21. The method of claim 1 comprising administering lacosamide and/or a pharmaceutically acceptable salt thereof and levetiracetam and/or a pharmaceutically acceptable salt thereof in amounts to provide an interaction index a greater than zero but less than about 0.7.

22. The method of claim 1 comprising administering lacosamide and/or a pharmaceutically acceptable salt thereof and levetiracetam and/or a pharmaceutically acceptable salt thereof in amounts to provide a benefit index for the combination of at least about 1.3.

* * * * *